United States Patent
Hollenbeck et al.

(10) Patent No.: US 9,897,535 B2
(45) Date of Patent: Feb. 20, 2018

(54) OPTICAL READER SYSTEMS AND METHODS FOR MICROPLATE POSITION DETECTION

(75) Inventors: Ronald C Hollenbeck, Elmira, NY (US); David Andrew Pastel, Horseheads, NY (US); Hak C. Sim, Painted Post, NY (US); Cameron J. Tovey, Painted Post, NY (US); Cynthia L. Wida, Elmira, NY (US)

(73) Assignee: Corning Incorporated, Corning, NY (US)

(*) Notice: Subject to any disclaimer, the term of this patent is extended or adjusted under 35 U.S.C. 154(b) by 575 days.

(21) Appl. No.: 13/356,956

(22) Filed: Jan. 24, 2012

(65) Prior Publication Data

US 2012/0212748 A1   Aug. 23, 2012

Related U.S. Application Data

(60) Provisional application No. 61/445,266, filed on Feb. 22, 2011.

(51) Int. Cl.
| | | |
|---|---|---|
| *G01J 3/447* | (2006.01) | |
| *G01B 11/00* | (2006.01) | |
| *G01J 3/30* | (2006.01) | |
| *G01B 11/14* | (2006.01) | |
| *G01N 21/00* | (2006.01) | |
| *G01N 21/25* | (2006.01) | |
| *G01N 21/77* | (2006.01) | |

(52) U.S. Cl.
CPC ....... *G01N 21/253* (2013.01); *G01N 21/7743* (2013.01)

(58) Field of Classification Search
CPC .... G01B 11/14; G01N 21/554; G01N 21/553; G01N 21/54373
USPC ........... 356/399–401, 614–624, 317, 326.31; 436/164–172; 422/82.05–82.09
See application file for complete search history.

(56) References Cited

U.S. PATENT DOCUMENTS

| 3,892,484 | A | * | 7/1975 | Tsuboshima et al. ........ 356/326 |
|---|---|---|---|---|
| 4,815,843 | A | | 3/1989 | Tiefenthaler et al. ........ 356/128 |
| 5,738,825 | A | | 4/1998 | Pfeifer ............................. 422/3 |
| 6,155,490 | A | | 12/2000 | Ackley |
| 7,424,187 | B2 | | 9/2008 | Montgomery et al. ......... 385/39 |
| 7,629,173 | B2 | | 12/2009 | Gollier et al. |
| 2003/0027327 | A1 | * | 2/2003 | Cunningham et al. .... 435/287.2 |

(Continued)

OTHER PUBLICATIONS

Locke White, Am. J. Phys. 33, 468 (1965) Low frequency circuit for Driving a galvanometer in forced linear oscillation.*

(Continued)

*Primary Examiner* — Sunghee Y Gray
(74) *Attorney, Agent, or Firm* — John P. Ciccarelli; John L. Haack

(57) ABSTRACT

Optical reader systems and methods with accurate microplate position detection capability are disclosed. The optical reader systems having scanning optical systems that are configured to scan select position-detecting features on the microplate to accurately determine their respective positions. The measurement of the positions of the position-detecting features can also be used to calibrate the optical reader system to reduce or eliminate adverse positioning effects from system non-linearities that arise from one or more of the system components, including the scanning optical system.

9 Claims, 18 Drawing Sheets

(56) References Cited

U.S. PATENT DOCUMENTS

| | | |
|---|---|---|
| 2004/0108447 A1* | 6/2004 | Curry et al. .................. 250/234 |
| 2006/0139641 A1* | 6/2006 | Gollier et al. ................ 356/399 |
| 2006/0141611 A1 | 6/2006 | Frutos et al. |
| 2006/0204402 A1* | 9/2006 | Tomaru ...................... 422/82.05 |
| 2006/0205058 A1 | 9/2006 | Frutos et al. ................ 435/287 |
| 2006/0269886 A1 | 11/2006 | Musa et al. |
| 2007/0016373 A1* | 1/2007 | Hunter et al. .................. 702/19 |
| 2007/0141567 A1* | 6/2007 | Wulfman et al. ................. 435/6 |
| 2007/0202543 A1 | 8/2007 | Gollier et al. ................ 435/7.1 |
| 2009/0159812 A1* | 6/2009 | Livingston ................... 250/428 |
| 2009/0247416 A1* | 10/2009 | Can et al. ........................ 506/7 |
| 2010/0049180 A1* | 2/2010 | Wells et al. ..................... 606/12 |
| 2011/0096326 A1* | 4/2011 | Crafts et al. ................. 356/326 |
| 2011/0102799 A1* | 5/2011 | Matejka et al. .............. 356/448 |
| 2011/0130969 A1* | 6/2011 | Gollier et al. .................. 702/19 |
| 2011/0188038 A1* | 8/2011 | Gollier et al. ................ 356/328 |

OTHER PUBLICATIONS

A&A 474, 679-687 (2007) DOI: 10.1051/0004-6361:20077811 The on the Fly imaging technique J.G. Mangum1—D. T. Emerson2—E.W. Greisen3.*

* cited by examiner

OPTICAL READER SYSTEMS AND METHODS FOR MICROPLATE POSITION DETECTION

This application claims the benefit of priority under 35 U.S.C. § 119 of U.S. Provisional Application Ser. No. 61/445,266, filed on Feb. 22, 2011, the content of which is relied upon and incorporated herein by reference in its entirety.

FIELD

The present disclosure relates to label-independent optical reader systems, and in particular to optical reader systems and methods with accurate microplate position detection.

BACKGROUND

Manufacturers of optical reader systems seek to design a new and improved optical reader systems that can be used to interrogate a resonant waveguide grating biosensor to determine if a biomolecular binding event (e.g., binding of a drug to a protein) occurred on a surface of the biosensor. Of present interest are optical reader systems and methods with improved position detection of the microplate that supports the biosensors to reduce variations in readings of the biosensors. Such new and improved optical reader systems and methods that have such capability are the subject of the present disclosure.

SUMMARY

Aspects of the disclosure are directed to optical reader systems and methods with accurate microplate position detection capability. The optical reader systems having scanning optical systems configured to scan select position-detecting features on the microplate to accurately determine their respective positions. This in turn allows for the microplate position to be accurately defined relative to a reference of the optical system. Such accurate position detection of the microplate enables accurate scan paths over the biosensor, leading to increased accuracy in reading the biosensors The measurement of the positions of the position-detecting features can also be used to calibrate the optical reader system to reduce or eliminate distortions and non-linearities that arise from one or more of the system components, including the scanning optical system.

In various examples, the scanning optical systems employ f-theta lenses. Also in examples, the scanning mirror devices include micro-electrical-mechanical system (MEMS) mirrors, which can have substantial non-linearity relative to the positioning requirements of scanning a biosensor.

The position-detecting systems and methods disclosed herein can provide fast and accurate determination of the position of features on the microplate surface using generally one-dimensional scan paths that include a general direction with an oscillating component generally perpendicular to the general scan path direction. The systems and methods benefit from the use of a photodetector configured for integrating the detected reflected light so that it measures an averaged result for sections of the oscillation component of the scan path.

The position-detecting systems and methods disclosed herein are useful where exhaustive two-dimensional mapping of a sample does not meet cycle time requirements because the photodetector is slow. Photodetector integration is combined with the oscillatory motion of the beam spot to slow-photodetector limitations.

These and other advantages of the disclosure will be further understood and appreciated by those skilled in the art by reference to the following written specification, claims and appended drawings.

BRIEF DESCRIPTION OF THE DRAWINGS

A more complete understanding of the present disclosure may be had by reference to the following detailed description when taken in conjunction with the accompanying drawings wherein.

DETAILED DESCRIPTION

Reference is now made to embodiments of the disclosure, exemplary embodiments of which are illustrated in the accompanying drawings.

In the discussion below, in certain descriptions, the angle θ is a "deflection angle" and refers to the angle of incident optical beams 134I relative to optical axis A1 as these optical beams leave scanning mirror device 260. Also in certain descriptions, the angle φ refers to an "incidence angle" that the incident optical beams 134I make relative to the surface normal N of microplate 170. Microplate 170 is assumed to lie in an X-Y plane thereby defining deflection angles $\theta_X$ and $\theta_Y$ and incident angles $\varphi_X$ and $\varphi_Y$ associated with incident optical beam(s) 134I. In certain descriptions, the angle θ is used in place of angle φ as described above, and one skilled in the art will understand from the context of the discussion the meaning of the particular symbol used for a given angle.

Optical Reader System

Figure 1:
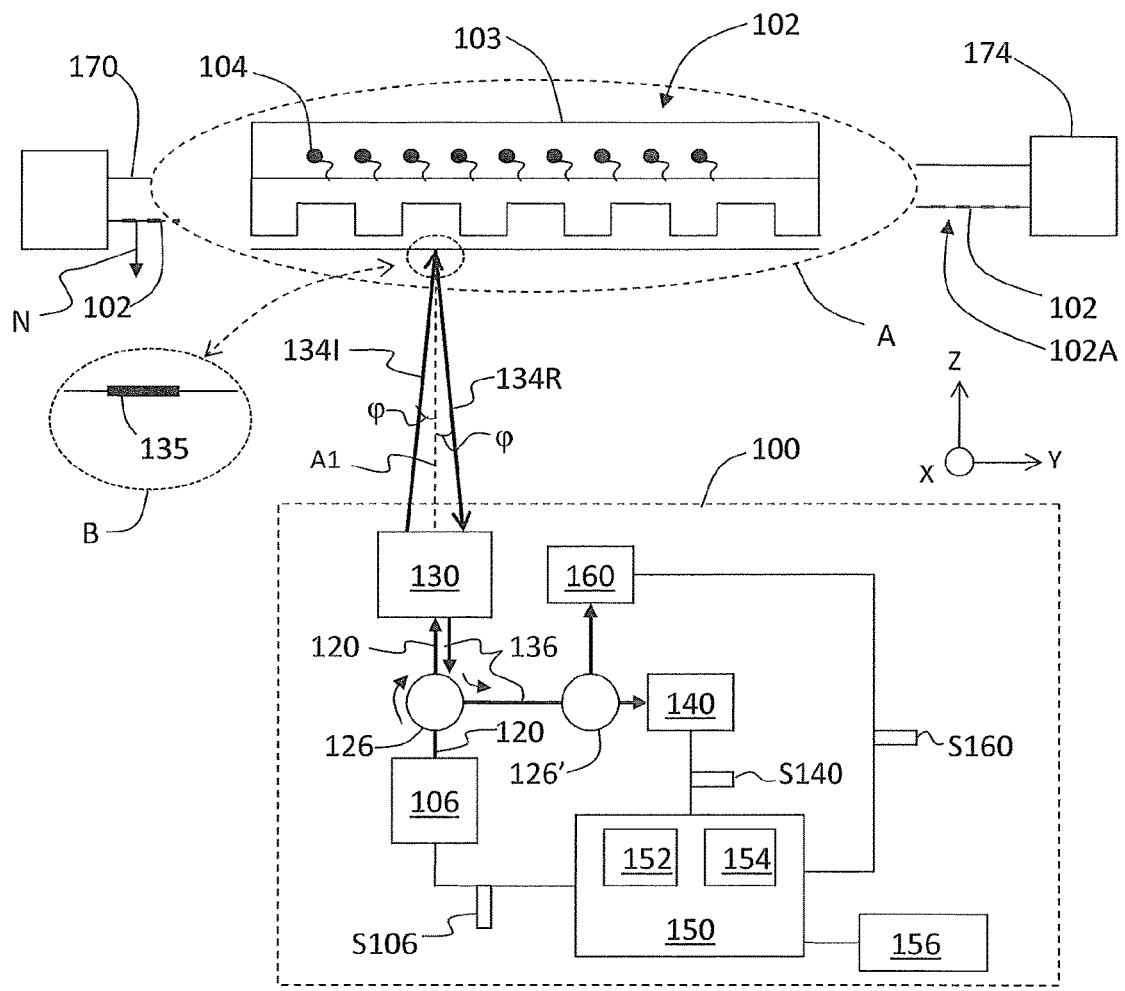
FIG. 1 is a generalized schematic diagram of an optical reader system of the disclosure.

FIG. 1 is a generalized schematic diagram of an optical reader system ("system") 100 of the present disclosure and used to interrogate one or more biosensors 102 each having a surface 103 to determine if a biological substance 104 is present on the biosensor. Inset A shows a close-up of an exemplary biosensor 102. Biosensor 102 may be, for example, a resonant waveguide grating (RWG) biosensor, a surface plasmon resonance (SPR) biosensor, or like biosensor. U.S. Pat. No. 4,815,843 describes example biosensors 102.

Figure 2:
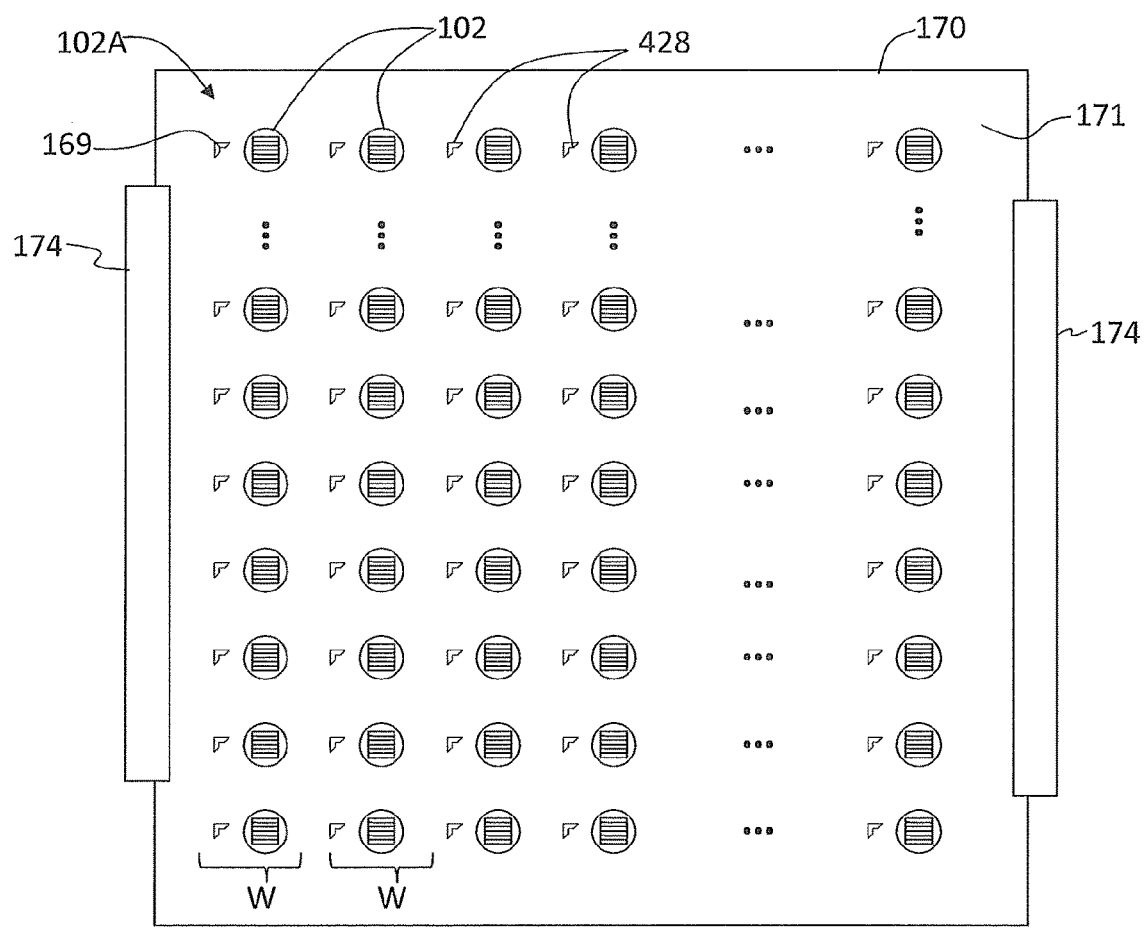
FIG. 2 shows an exemplary biosensor array operably supported in regions or "wells" of a microplate, which in turn is held by a microplate holder.

FIG. 2 shows an exemplary configuration where biosensors 102 are arranged in an array 102A and operably supported in regions or "wells" W of a microplate 170 having a surface 171. An exemplary biosensor array 102A has a 4.5 mm pitch for biosensors 102 that are 2 mm square, and includes 16 biosensors per column and 24 biosensors in each row. In an example, microplate 170 includes fiducials 169 on microplate surface 171 that can be used to position, align, or both the microplate 170 in system 100 relative to a reference location. A microplate holder 174 is also shown holding microplate 170. Many different types of plate holders can be used as microplate holder 174. U.S. Pat. No. 5,738,825 describes example microplates 170.

With reference again to FIG. 1, optical reader system 100 includes a light source assembly 106 (e.g., lamp, laser, diode, filters, attenuators, etc.) that generates light 120. Light 120 is directed by a coupling device 126 (e.g., a circulator, optical switch, fiber splitter or the like) to a scanning optical system 130 that has an associated optical axis A1 and that transforms light 120 into an incident optical beam 134I, which forms a beam spot 135 at biosensor 102 (see inset B). Incident optical beam 134I (and thus beam spot 135) is scanned over the biosensor 102 by the operation of scanning optical system 130. In an example, the biosensor 102 is moved (i.e., by moving microplate 170) so that the incident optical beam can be scanned across the biosensor 102. Also in an example, the incident optical beam 134I is scanned across a stationary biosensor 102 using scanning optical system 130, as described further below. In another example, both scanning and microplate movement can be employed.

Incident optical beam 134I reflects from biosensor 102, thereby forming a reflected optical beam 134R. Reflected optical beam 134R is received by scanning optical system 130 and light 136 therefrom (hereinafter, "guided light signal") is directed by coupling device 126 to a spectrometer unit 140, which generates an electrical signal S140 representative of the spectra of the reflected optical beam. In embodiments, a controller 150 having a processor unit ("processor") 152 and a memory unit ("memory") 154 then receives electrical signal S140 and stores in the memory the raw spectral data, which is a function of a position (and possibly time) on biosensor 102.

Figure 3:
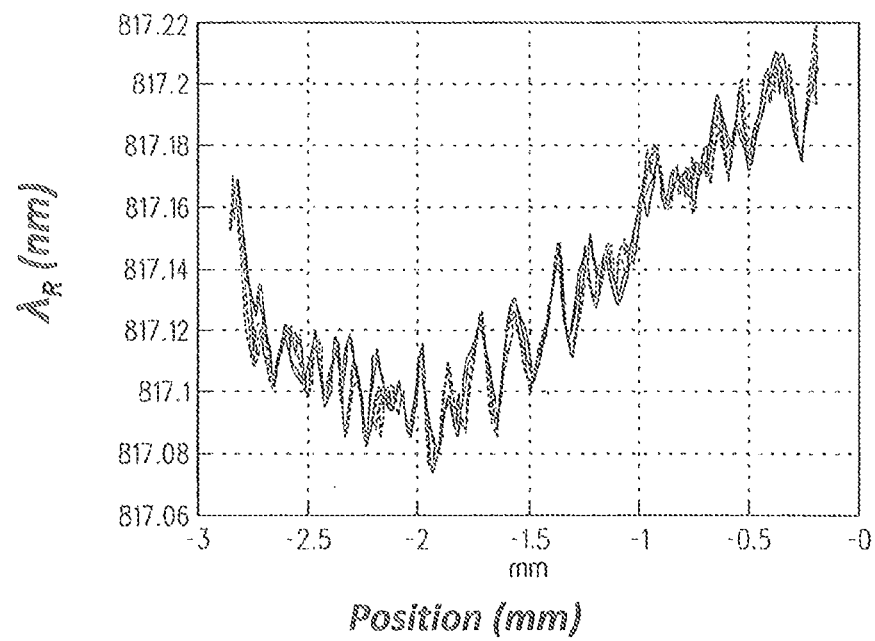
FIG. 3 is a plot of resonant wavelength $\lambda_R$ (nm) vs. position (mm) across the biosensor.

Thereafter, processor 152 analyzes the raw spectral data based on instructions stored therein or in memory 152. The result is a spatial map of resonant wavelength ($\lambda_R$) data such as shown by way of illustration in FIG. 3, which shows the calculated resonance centroid as a function of the position of the scanning spot across the sensor for a number of different scans. The variation of the resonance wavelength indicates if a chemical or biological reaction happened for a specific sensor.

In embodiments, controller 150 includes or is operably connected to a display unit 156 that displays measurement information such as spectra plots, resonant wavelength plots, and other measurement results, as well as system status and performance parameters. In another embodiment, spectra can be processed immediately so that only the wavelength centroid is stored in memory 154.

Also in example, system 10 includes a photodetector 160 used to detect the intensity of reflected optical beam 134R without the reflected optical beam passing to spectrometer 140. This configuration is useful when performing diagnostic measurements or for determining the position of microplate 170 using the positioning methods described in greater detail below. In an example, photodetector 160 is operably connected to a second circulator 126' located between first circulator 126 and spectrometer 140. Photodetector 160 generates a photodetector signals S160 that is provided to controller 150 and is processed using, for example, processor 152 therein. Intensity data from photodetector 160 can also be stored in memory 154.

Biosensors

Example biosensors 102 make use of changes in the refractive index at sensor surface 103 that affect the waveguide coupling properties of incident optical beam 134I and reflected optical beam 134R to enable label-free detection of biological substance 104 (e.g., cell, molecule, protein, drug, chemical compound, nucleic acid, peptide, carbohydrate) on the biosensor. Biological substance 104 may be located within a bulk fluid deposited on biosensor surface 103, and the presence of this biological substance alters the index of refraction at the biosensor surface.

To detect biological substance 104, biosensor 102 can be probed with incident optical beam 134I while reflected optical beam 134R is received at spectrometer unit 140. Controller 150 can be configured (e.g., processor 152 can be programmed) to determine if there are any changes (e.g., 1 part per million) in the biosensor refractive index caused by the presence of biological substance 104. In embodiments, biosensor surface 103 can be coated with, for example, biochemical compounds (not shown) that only allow surface attachment of specific complementary biological substances 104, thereby enabling biosensor 102 to be both highly sensitive and highly specific. In this way, system 100 and biosensor 102 can be used to detect a wide variety of biological substances 104. Likewise, biosensor 102 can be used to detect the movements or changes in cells immobilized to biosensor surface 103, for example, when the cells move relative to the biosensor or when they incorporate or eject material a refractive index change occurs.

If multiple biosensors 102 are operably supported as an array 102A in wells W of microplate 170, which in turn is supported by microplate holder 174, then they can be used to enable high-throughput drug or chemical screening studies. For a more detailed discussion about the detection of a biological substance 104 (or a biomolecular binding event) using scanning optical reader systems, reference is made to U.S. Patent Application Publication No. 2006/0141611. Other optical reader systems are described in U.S. Pat. No. 7,424,187 and U.S. Patent Application Publications No. 2006/0205058 and 2007/0202543.

Spectral Interrogation

The most commonly used technique for measuring biochemical or cell assay events occurring on RWG-based biosensors 102 is spectral interrogation. Spectral interrogation entails illuminating biosensor 102 with a multi-wavelength or broadband beam of light (incident optical beam 134I), collecting the reflected light (reflected optical beam 134R), and analyzing the reflected spectrum with spectrometer unit 140.

Figure 4:
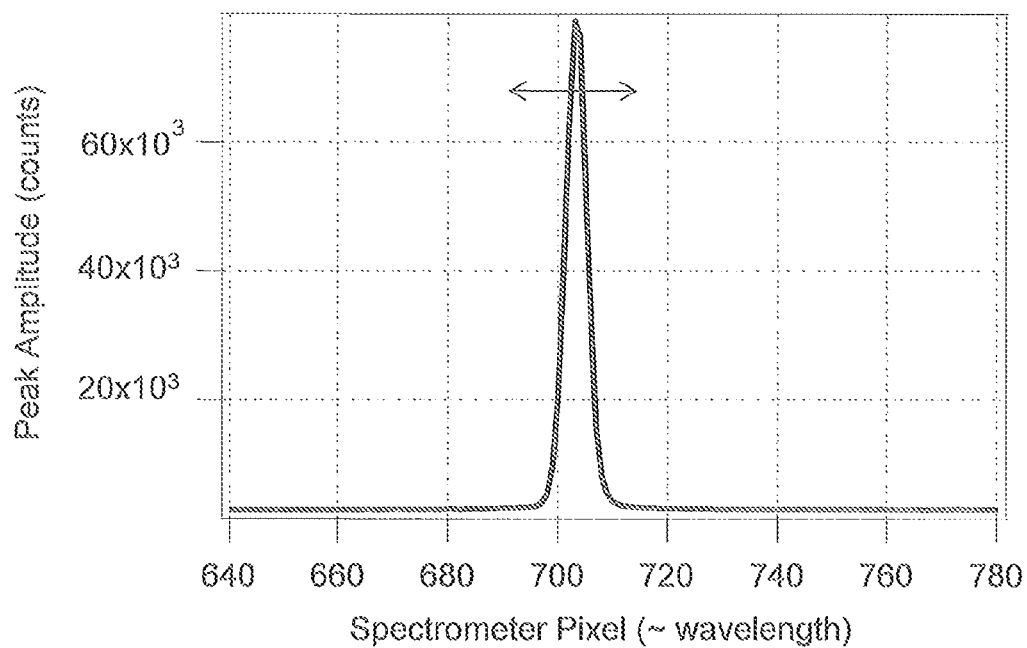
FIG. 4 is a plot of the peak amplitude (photon counts) versus spectrometer pixel location, which corresponds to wavelength.

An exemplary reflection spectrum from an example spectrometer unit 140 is shown in FIG. 4, where the "peak amplitude" is the number of photon counts as determined by an analog-to-digital (A/D) converter in the spectrometer. When chemical binding occurs at biosensor surface 103, the resonance shifts slightly in wavelength as indicated by the double arrow, and this shift can be detected by spectrometer unit 140.

While the general concept of spectral interrogation of biosensor 102 is straightforward, the implementation details of how light can be delivered to and collected from the biosensor can have a major impact on the quality of the data and practical utility of system 100. For example, due to inevitable non-homogeneity of the resonant wavelength $\lambda_R$ across biosensors 102, the measured resonant wavelength $\lambda_R$ is extremely sensitive to the position of incident optical beam 134I over the biosensor.

Further, variation in absolute readings between microplates 170 is large compared with the wavelength shift. There can be significant differences between absolute readings of biosensors 102 on the same microplate, between microplates, and between readings of the same microplate taken by two different optical readers. Optical readers currently need at least two readings to detect activity. The reported measurement is a wavelength shift between the current condition and an earlier "baseline" condition, such as before the addition of biological substance 104, such as cells or proteins. Typically, microplate 170 needs to be removed and repositioned between some measurements to add reagents or so that other microplates 170 can be measured while the reagents take effect. This typically leads to errors in plate position, which in turn causes errors in the reading of biosensors 102.

Biosensors 102 are also inherently non-homogeneous due to manufacturing processes used to make them. For example, there is typically a variation in the absolute resonant wavelength within each biosensor. Consequently, any wavelength shift between readings of a biosensor can only be attributed to biochemical change if the same point(s) on the biosensor are measured. An error of 0.01 mm in the position of beam spot 135 on biosensor 102 can cause a wavelength shift large enough to be mistaken for biological activity. Optical readers thus need to account for this non-homogeneity in order for the measurements to be repeatable. It is therefore desirable that microplate positioning within the optical reader be as accurate as possible. This requires both position detection capability and positioning capability, which are discussed in greater detail below.

Single-Channel Scanning Optical Reader System

Figure 5:
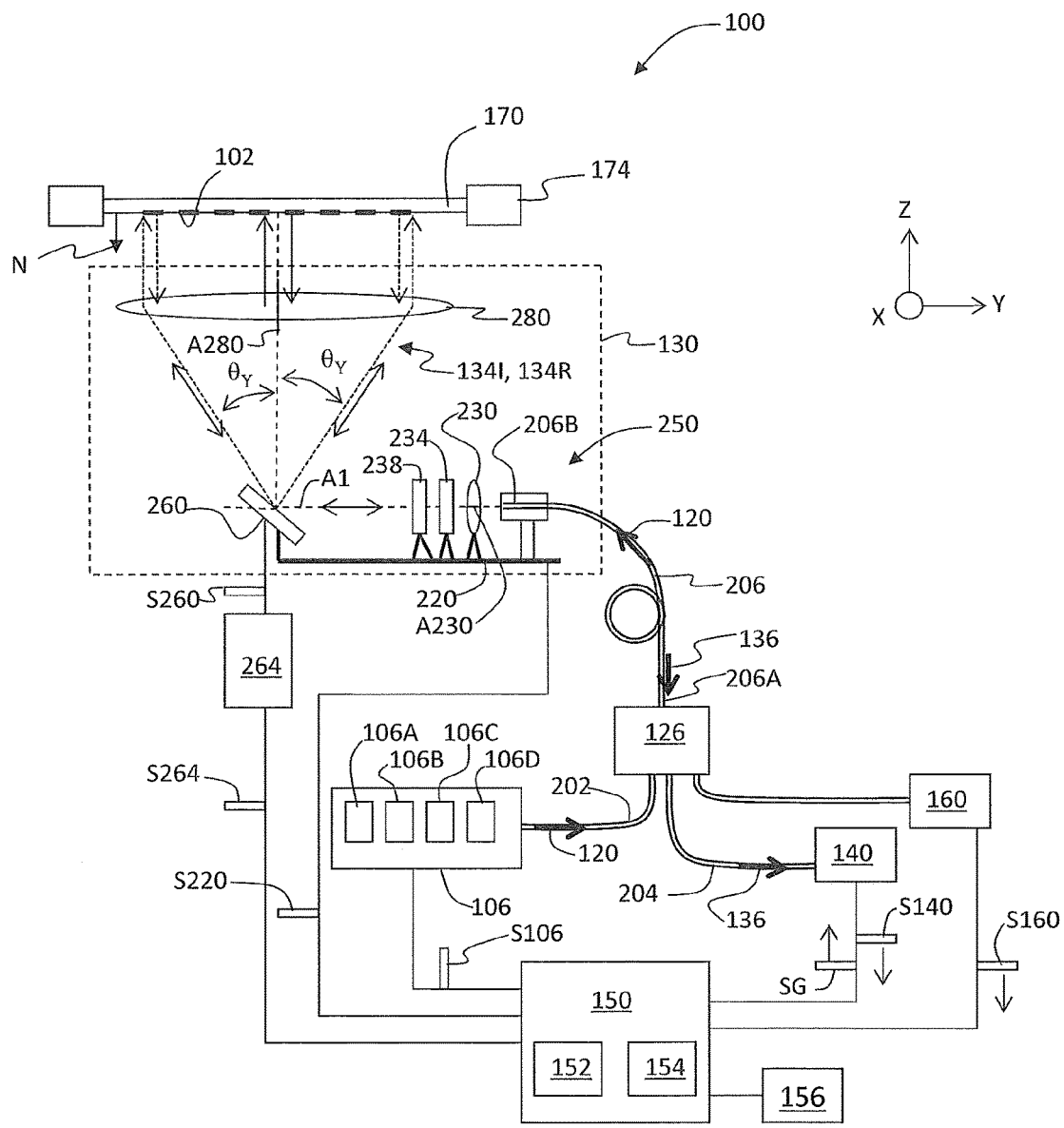
FIG. 5 is a detailed schematic diagram of a single-channel embodiment of a scanning optical reader system of the disclosure.

FIG. 5 is a detailed schematic diagram of an example single-channel embodiment of system 100. Cartesian X-Y-Z coordinates are shown for reference. An exemplary light source assembly 106 comprises a light source 106A, a variable optical attenuator 106B, a polarization scrambler 106C and an optical isolator 106D. Polarization scrambler 106C serves to randomize the polarization of light 120, and optical isolator 106D serves to prevent scattered or reflected light from returning to light source 106A.

An exemplary light source 106A includes a wide spectrum source such as a superluminous diode (SLD). Light source assembly 106 is optically connected by a first optical fiber section 202 to coupling device 126, which in the present embodiment is a 1×2 fiber splitter. Spectrometer unit 140 comprises a spectrometer, such as an HR-2000 spectrometer, available from Ocean Optics, Dunedin, Fla. Spectrometer unit 140 can be connected by a second optical fiber section 204 to coupling device 126. A third optical fiber section 206 can be connected at one end 206A to coupling device 126, while the other end portion 206B can be mounted on a X-Y-Z translation stage 220.

Also mounted on translation stage 220 can be a focusing lens 230 having a focal length f2, a linear polarizer 234 and a quarter-wave plate 238. Note that focusing lens 230 may comprise one or more optical elements. Fiber section end 206A, focusing lens 230, linear polarizer 234 and quarter-wave plate 238 constitute an adjustable beam-forming optical system 250 that shares the aforementioned optical axis A1.

In embodiments, translation using translation state 220 can be accomplished manually, while in other embodiments can be accomplished automatically under the control of controller 150 via a control signal S220. In an exemplary embodiment, the first, second, and third fiber sections 202, 204 and 206 can be single-mode (SM) fiber sections.

Figure 6:
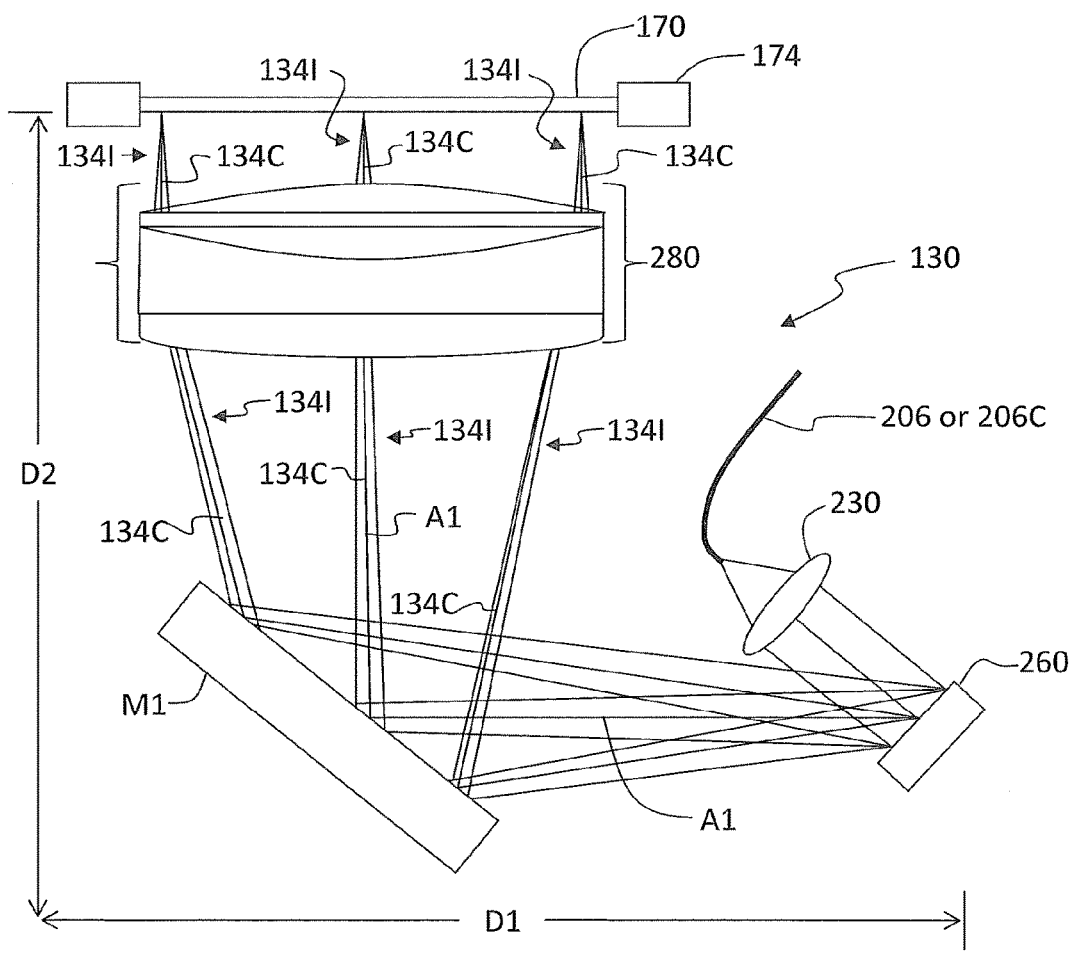
FIG. 6 is a close-up schematic diagram of an exemplary scanning optical system that includes a scanning mirror device, a fold mirror, and an f-theta focusing lens.

System 100 includes a scanning mirror device 260 arranged along optical axis A1 adjacent beam-forming optical system 250. FIG. 6 is a close-up schematic diagram of an exemplary scanning optical system 130 that includes beam-forming optical system 250 and scanning mirror device 260. Scanning mirror device 260 can be, for example, a micro-electro-mechanical system-(MEMS)-based mirror, such as is available from Mirrorcle Technologies, Inc., Albany, Calif., or from Texas Instruments, Dallas, Tex., as model TALP 1011, for example. Other exemplary embodiments of scanning mirror device 260 can include a scanning galvanometer, a flexure-based scanning mirror, an oscillating plane mirror, a rotating multifaceted mirror, and a piezo-electric-driven mirror.

Scanning mirror device 260 can be adapted to scan in at least one dimension (1D) and preferably two-dimensions (2D) (i.e., along axes X and Y, thereby defining associated scanning angles $\theta_X$ and $\theta_Y$). Scanning mirror device 260 can be operably connected to a mirror device driver 264, which may be based on voltage or current depending on the nature of scanning mirror device 260. In embodiments, scanning mirror device 260 can be mounted on translation stage 220.

A field lens 280 can be arranged along optical axis A1 adjacent scanning mirror device 260 and opposite beam-forming optical system 250. In embodiments, field lens 280 has an F-theta configuration wherein light from any angle θ is directed substantially parallel to optical axis A1 (i.e., φ~0°). Suitable F-theta field lenses 280 are commercially available from optics suppliers, such as Edmund Optics, Barrington, N.J. Field lens 280 has a focal length f1 and comprises at least one optical element. In embodiments, field lens 280 comprises multiple optical elements, including at least one mirror, or at least one lens, or a combination of at least one mirror and at least one lens. In an exemplary embodiment, field lens 280 includes one or more aspherical surfaces.

System 100 also includes the aforementioned microplate holder 174 configured to operably support microplate 170, which in turn is configured to operably support an array of biosensors 102. In an exemplary embodiment, the position of microplate holder 174 is adjustable so that the position of microplate 170 can be adjusted relative to optical axis A1. Scanning mirror device 260 is located at the focus of field lens 280, i.e., at a distance f1 from the field lens.

System 100 of FIG. 5 is also configured in an example with aforementioned photodetector 160 optically connected to circulator 126.

System 100 of FIG. 6 illustrates an exemplary scanning optical system 130 shown optically coupled to beam-forming optical system 250 and that includes scanning mirror device 260, a fold mirror M1, and f-theta field lens 280. Also shown is microplate holder 174 with microplate 170 supported thereby. Fold mirror M1 can be used to fold optical axis A1 and thus fold the optical path to make scanning optical system 130 more compact. In embodiments, focusing lens 230 has a focal length f2=10 mm and field lens 280 has a focal length f1=200 mm with an aperture of 72 mm. This particular configuration for scanning optical system 130 fits within dimensions L1×L2=140 mm×140 mm and thus has a relatively compact form factor. In embodiments, beam-forming optical system 250 can be included in scanning optical system 130.

The size of the microplate 170 that can be scanned by scanning mirror device 260 is given by the tangent of the mirror deflection multiplied by the focal length of the field lens 280. So, with +/−10 degrees of optical deflection and a 200 mm focal length field lens 280, a 72 mm area can be scanned in both the X- and Y-directions.

An exemplary scanning optical system 130 of FIG. 6 is capable of interrogating a single microplate column of biosensors 102 when configured in a standard microplate format of sixteen wells per column on a 4.5 mm pitch, or about a 72 mm total distance. An exemplary nominal size of beam spot 135 formed by incident optical beam 134I at microplate 170 is 0.1 mm at $1/e^2$ (diameter) and an exemplary beam diameter of the incident optical beam at scanning mirror device 260 is 2 mm at $1/e^2$. FIG. 6 illustrates incident optical beam 134I at three different scan positions (angles). The central ray of incident optical beam 134I is denoted 134C. Note the incident optical beam 134I is a converging beam at microplate 170, with the central rays 134C being parallel to optical axis A1 at the microplate.

As discussed above, exemplary scanning mirror device 260 is a MEMS-based mirror (such as the aforementioned TALP1011 from Texas Instruments), which in an example has a clear aperture of 3.2 mm×3.6 mm and optical scanning angles $\theta_X$ and $\theta_Y$ of +/−10°. The variation of incidence angle φ of incident optical beam 134R over microplate 170 due to aberrations in an exemplary field lens 280 was found in one example system 100 to be less than 0.3 mRd.

Controller 150 is operably connected to light source assembly 106, spectrometer unit 140 and mirror device driver 264, and is configured (e.g., via software embodied in a computer readable medium such as in processor 152 or memory 154) to control the operation of system 100 as described below. In embodiments, controller 150 can be configured with a General Purpose Interface Bus (GPIB) and the devices to which the controller is operably connected can be configured to communicate with the controller using the GPIB.

With reference again to FIG. 5, in the general operation of system 100, controller 150 sends a light source control signal S106 to light source assembly 106 to cause the light source assembly to generate light 120, which is coupled into first fiber section 202 as guided light. Light 120 travels down first fiber section 202 and to third fiber section 206 via coupling device 126. Light 120 is then processed by beam-forming optical system 250, which forms incident optical beam 134I. Incident optical beam 134I is then selectively deflected by scanning mirror device 260 under the operation of a control signal S260 from mirror device driver 264, which in turn is activated by a control signals S264 from controller 150.

Because scanning mirror device 260 is located at the focus of field lens 280, in the region between the field lens and microplate, the incident optical beam 134I (or, more precisely, the central ray 134C of this beam) is parallel to optical axis A1 for all deflection angles. System 100 can be adjusted so that incident optical beam 134I remains substantially normal to microplate 170 as the beam scans the microplate.

Incident optical beam 134I scans over biosensor 104 as described below and reflects therefrom at substantially normal incidence to form reflected optical beam 134R. Reflected optical beam 134R thus travels substantially the reverse optical path of incident optical beam 134I and is coupled back via beam-forming optical system 250 into third fiber section 206 at end portion 206B and becomes guided light signal 136. Guided light signal 136 then travels through third optical fiber section 206 to second optical fiber section 204 via coupling device 126, where it is received and spectrally decomposed by spectrometer unit 140. Spectrometer unit 140 provides electrical signal S140 representative of the spectral information in reflected optical beam 134R to controller 150 and to memory 154 therein. Memory 154 stores the spectral information as a function of the scanning angles ($\theta_X$, $\theta_Y$). In embodiments, memory 154 stores and processor 152 runs analysis software for analyzing and visualizing the spectral information, such as Matlab, available from Mathworks, Inc., Natick, Mass.

In embodiments, memory 154 stores a number (e.g., 50) of spectra for each biosensor 102, and processor 152 sums the spectra to obtain a total spectra, and then calculates the centroid to determine resonant wavelength $\lambda_R$. In embodiments, tens, hundreds, or thousands of spectra can be saved in memory 154 for processing by processor 152. Spectra measurements can be divided up by, for example, individual biosensors 102 or by columns or rows of biosensors.

Biosensor Scanning

One method of scanning using system 100 is to operate scanning mirror device 260 to scan one or more biosensors 102 in a single scanning direction. However, a shortcoming of this approach is that the resonance wavelength $\lambda_R$ varies significantly as a function of the position of beam spot 135 across biosensor 102. Accordingly, in this approach the position of beam spot 135 needs to be monitored closely to avoid introducing measurement bias.

A preferred method of operating system 100 involves scanning biosensors 102 with incident optical beam 134I in two dimensions X and Y to obtain an integrated measurement of each scanned biosensor. Because a MEMS-based mirror scanning device can be driven at a relative high frequency (e.g., ≥100 Hz), it is possible to rapidly perform such a two dimensional scan of a sensor. In one example, biosensor 102 is scanned by moving optical beam 134I (and thus beam spot 135) faster in one of the two dimensions to obtain a zig-zag or sinusoidal scan path.

In embodiments, system 100 can be configured so that the position of field lens 280 is adjustable relative to scanning mirror device 260 and beam-forming optical system 250. In embodiments, the relative positions of field lens axis A280, scanning mirror device 260 and focusing lens axis A230 are adjustable, i.e., one or more of these elements is displaceable relative to optical axis A1. In embodiments, this adjustability is provided by translation stage 220. The angle of incidence φ of incident optical beam 134I relative to microplate 170 is defined by the vector joining the center of the incident optical beam at focusing lens 230 and the apex of field lens 280.

Thus, in embodiments, incidence angle φ of incident optical beam 134I can be adjusted by adjusting the relative position of lenses 230 and 280. Such adjustment can be made in embodiments by adjusting translation stage 220 that includes scanning mirror device 260 and focusing lens 230. This operation does not require translation stage 220 to have high precision. By way of example, for a field lens 280 having a focal length f1=200 mm, the alignment precision only needs to be in the order of 0.2 mm to insure that the precision of incidence angle φ is within 1 mrad. This adjustability makes system 100 substantially insensitive to microplate misalignment.

Microplate Position Detection

The use of a MEMS-based scanning mirror device 260 provides certain performance and size advantages for optical reader system 100. However, such a scanning mirror device is not particularly precise. MEMS-based scanning mirror devices can have significant part-to part variations, are sensitive to temperature, and are only linear to about 5%. Where MEMS-based scanning mirror devices have positional feedback, its positioning ability can be considered coarse relative to the positioning capability needed for optical readers. However, a given MEMS-based scanning mirror devices can provide very repeatable positioning at a given temperature.

As discussed above, scanning mirror device 260 scans biosensor columns (or rows) by moving incident beam 134I and the attendant beam spot 135 nominally through the center of biosensors 102. The lack of precision of a MEMS-based scanning mirror device 260 is compensated by rapidly oscillating beam spot 135 in a direction normal to the scan direction so that substantially the entire biosensor 102 is covered. Typically, the spectrometer obtains an integrated (i.e. summed) response from one or more complete passes of the oscillation. The passes represent (beam-width) cross-sections that are numerically integrated.

This scanning method reduces but does not eliminate the above-described positional sensitivity issues. To substantially reduce or eliminate positional sensitivity, system 100 needs to measure an equal contribution from each point on the biosensor. To accomplish this, a number of conditions are satisfied.

The first condition is that velocity of beam spot 135 needs to be constant, as different dwell times on bio sensor 102 result in different measurement contributions from the different points on biosensor.

The second condition is that there be no changes in the relative illumination of beam spot 135 in between passes. For a beam spot 135 with uniform intensity, this condition can be achieved with perfectly vertical passes that just touch each other without overlap and without any gaps.

Where the scan path of beam spot 135 over biosensor 102 has a sine-wave (oscillating) pattern, the beam spot velocity is not constant. Also, spacing between measurements in the scan direction is larger between measurements near the top of the scan path than at the center. In addition, the intensity of beam spot 135 is not uniform and typically has a Gaussian intensity profile, so that a scan path with vertical sections and performed at a perfectly constant velocity cannot be properly spaced to give the desired uniform illumination.

For system 100 to overcome the positional errors of microplate 170 using the above-described scanning approach, scanning mirror device 260 would need to oscillate far faster (e.g., at least 50 times faster), and the spectrometer would need to sample far faster (e.g., over 5000 times faster). In addition, spatial information obtained by an area scanner in the direction of oscillation is applicable to the MEMS mirror response at that frequency, and since the frequency response of MEMS mirrors is usually not flat, the information cannot be used to move the beam to a static level in that direction. Thus, in short, the above-described light-spot scanning approach has its limitations in achieving improved measurement resolution in the face of the aforementioned microplate positioning sensitivities.

Accordingly, an aspect of the disclosure includes system 100 being configured for fast and accurate position detection of microplate 170. The position detection system and methods described herein generally include searching for and detecting select position-detecting features ("features") 300 on microplate 170 using scanned beam spot 135. The reflected light is detected, and the detected signal allows the features to be distinguished from the background. In an example, the detected features are the biosensors 102 and the background is the otherwise flat microplate surface 171. In another example, features 300 include fiducials 160.

Since features 300 are accurately placed on microplate 170 (i.e., their positions are by definition very accurately known), the relative position of microplate 170 can be accurately determined by measuring the locations of one or more features 300. This in turn allows for accurate scanning of beam spot 135 over the biosensor, to increase the performance of system 100.

The position detection methods disclosed herein can fall into one or both of two general categories: Those that use a scan path having an oscillating component added to a generally one-dimensional component to enhance the otherwise one-dimensional feature scan, and those that use the results of a previous search to define a new feature scan.

Figure 7:
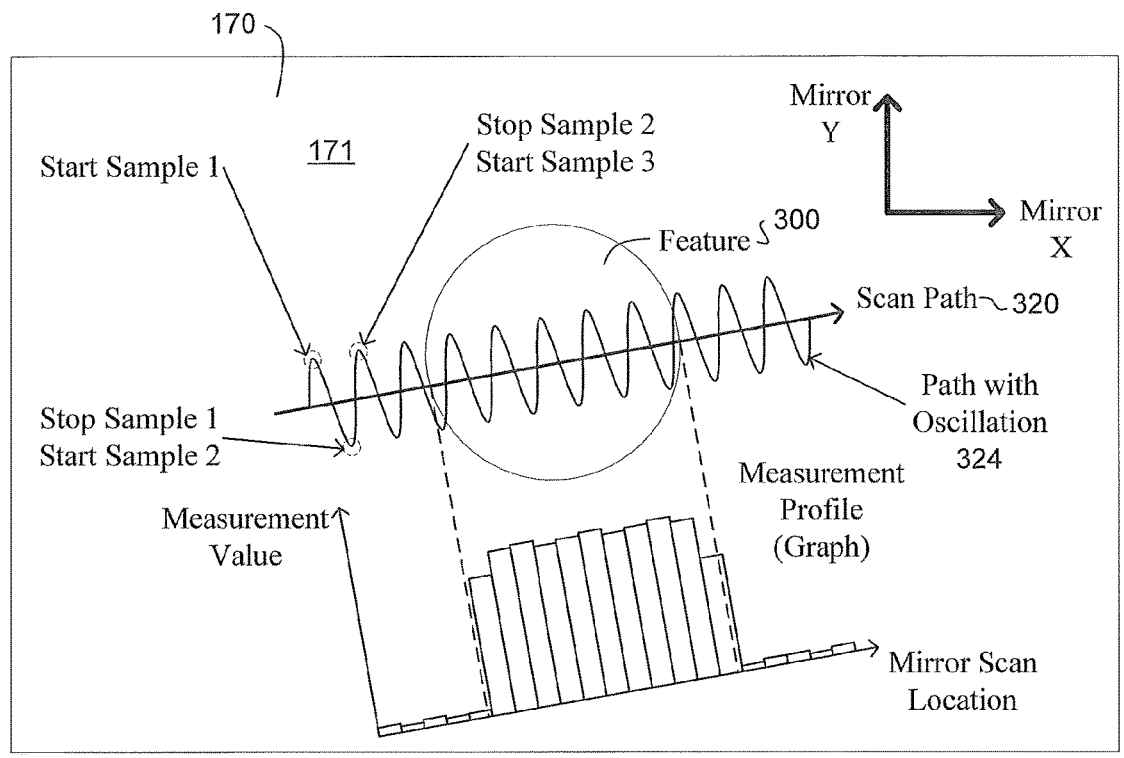
FIG. 7 is a schematic diagram that illustrates an example of a first position detection method for determining the position of microplate.

FIG. 7 is a schematic diagram that illustrates an example of a first position detection method for determining the position of microplate 170. Shown in FIG. 7 is a feature 300 located on microplate 170. Feature 300 can be, for example, biosensor 102 or the aforementioned fiducial 169. Using for example incident light beam 134I, beam spot 135 is positioned at a location on microplate surface 171 using for example scanning optical system 130. Beam spot 135 is moved in a general scan path direction (i.e., linear component) 320. As beam spot 135 is moved in the general scan path direction, it is oscillated in the perpendicular direction to impart an oscillatory component in forming the overall scan path 324. The oscillatory component can be sinusoidal, as shown. As scan path 324 crosses feature 300, reflected light 134R therefrom is directed to photodetector 160 to obtain a measured feature profile. In an example, the measured feature profile is established by relating the detected intensity in reflected light 134R to the location of beam spot 135 as determined by the corresponding mirror orientation of scanning mirror device 260. The plot in FIG. 7 illustrates an example of a measured feature profile for a feature 300 having substantially uniform reflectivity at the wavelength of incident and reflected light beams 134I and 134R.

In an example, multiple scans along the same direction can be performed using, for example, different oscillation amplitudes in the oscillation component of the scan path. In an example, photodetector 160 integrates by sampling reflected light beam 134R at a select sampling interval. The dashed lines accompanying the measured profile plot in FIG. 7 show where the edges of feature 300 reside, with the plot showing the integrated measurement between one time point to the next time point for the corresponding portion of the oscillating scan path 324. The measured profile of feature 300 can be further defined by taking readings from one (or more) oscillation passes, e.g., over different sections of the feature.

In an example, the center of feature 300 can be found by determining the feature edge locations and taking the halfway point, or by finding the center of the signal as represented by the plot of the measured profile, e.g., by measuring the centroid or using a similar center-finding technique.

Figure 8:
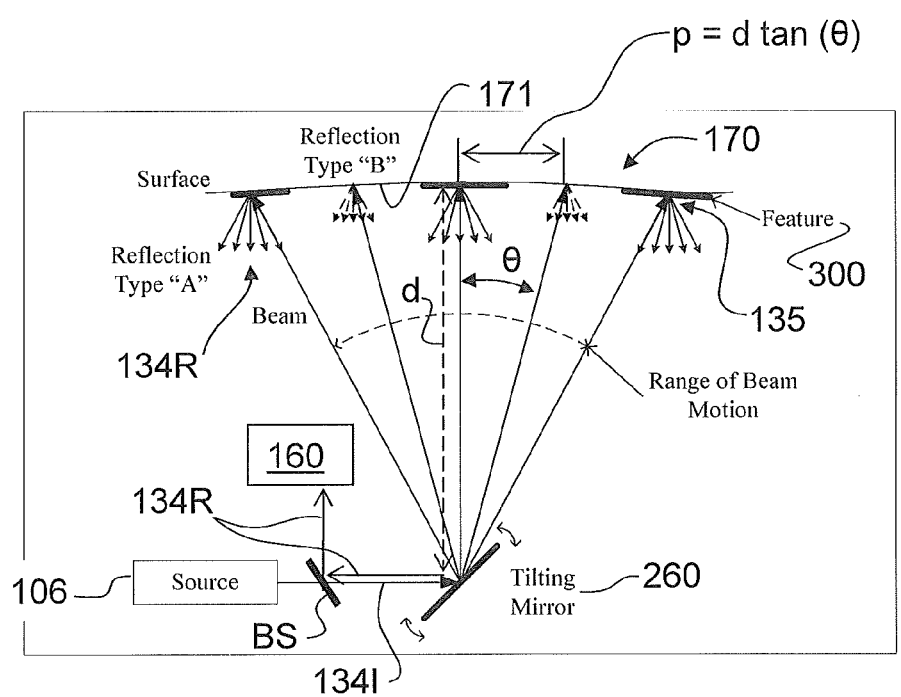
FIG. 8 is a schematic diagram of optical scanning system as used to measure the position of position-detecting features on the microplate.

FIG. 8 is a schematic diagram of optical scanning system 130 as used to measure the position of features 300 on microplate 170. As described above in connection with the operation of system 100 in reading biosensors 102, now system 100 is reading features 300, which can be the biosensors, fiducials 169, or any other type of reference features that can provide accurate position information about microplate 170 relative to a reference location of system 100. Thus, as described above, incident beam 134I from light source 106 is directed by scanning mirror device 260 generally to microplate 170 to be incident up microplate surface 171.

The beam angular range is controlled by controlling scanning mirror device with mirror device driver 264 (see FIG. 5), which can be programmed (or operated via controller 150) so that the mirror configuration (e.g., micromirror configuration of a MEMS-based mirror) correspond to positions on microplate 170. Scanning mirror device 260 scans beam spot 135 over scan path 324. Detector 160 can determine, via the detection of reflected light 134R, whether beam spot 135 scans over a feature 300 or background, which here is assumed to be the planar microplate surface 171 with a different reflectivity than the feature. This allows for scanning optical system 130 to detect the location of features 300, which leads to establishing an accurate microplate position.

Figure 9A:
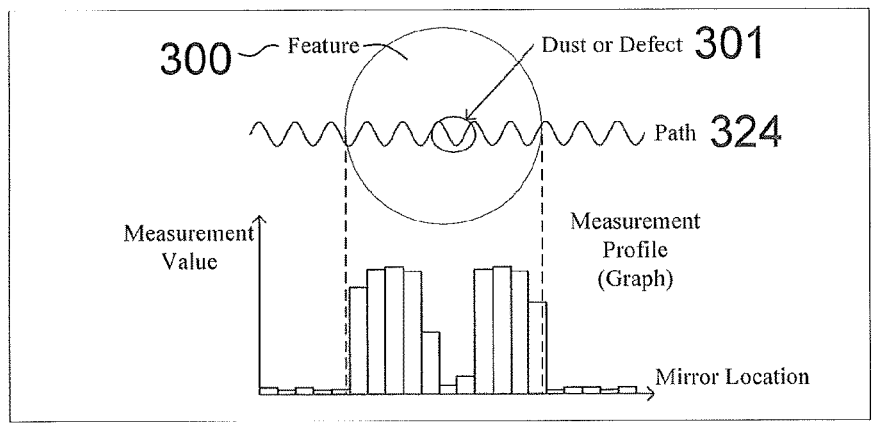
FIGS. 9A and 9B are schematic diagrams that illustrate two different scan paths having different oscillation amplitudes.
Figure 9B:
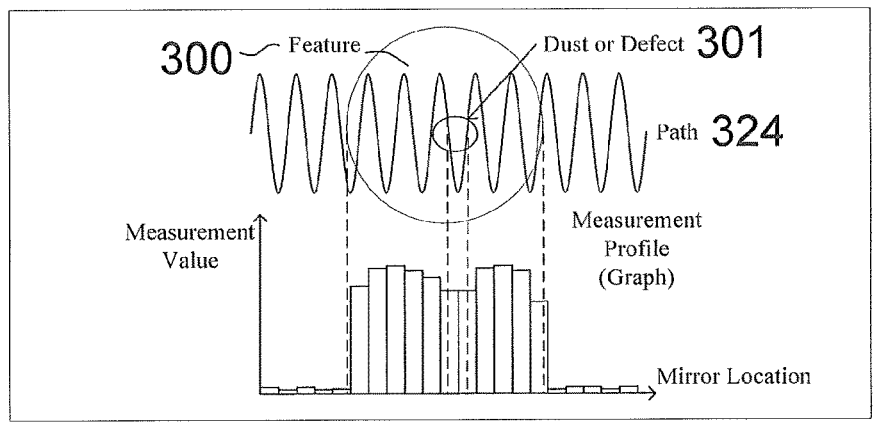

An aspect of the positioning systems and methods disclosed herein account for variations in the reflectivity of feature 300 due to any number of reasons, including for example the presence of debris or a defect 301 in the feature. FIGS. 9A and 9B are schematic diagrams that illustrate two different scan paths 324 having different oscillation amplitudes. Note how increasing the scan path oscillation amplitude allows for feature 300 to be detected as a single feature rather than as two features despite the presence of defect 301. Thus, the "hole" that was present in the plot of the "measurement value" (i.e., detected intensity) vs. mirror location (i.e., mirror configuration) of FIG. 9A shows up as a much smaller measurement variation that indicates a single feature 300 rather than two separate features. Thus, by finding the feature edges in the measured feature profile as described above, the center of the feature can be determined even though the feature has a defect or contaminant 301.

Figure 10A:
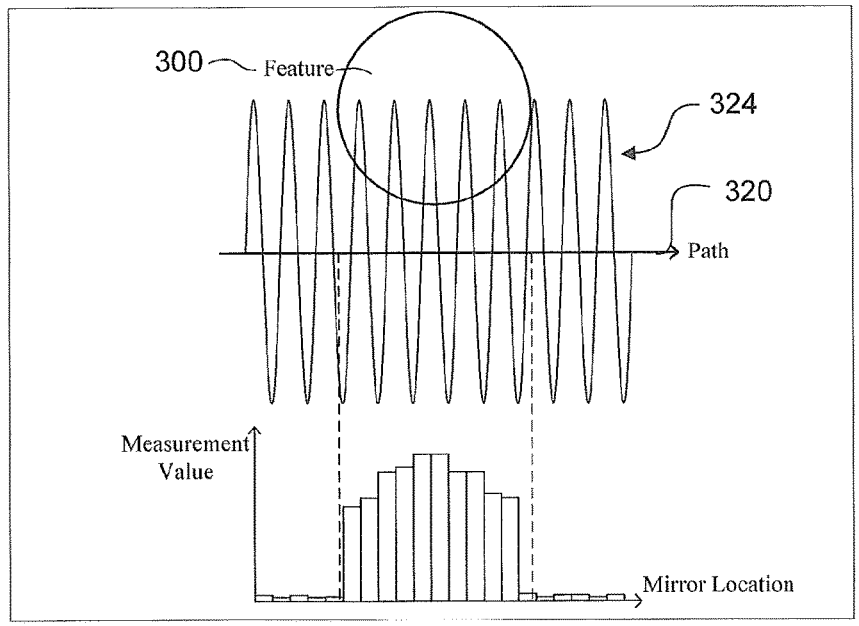
FIG. 10A and FIG. 10B illustrate an example position detection method where the scan path oscillation amplitude is made relatively large.
Figure 10B:
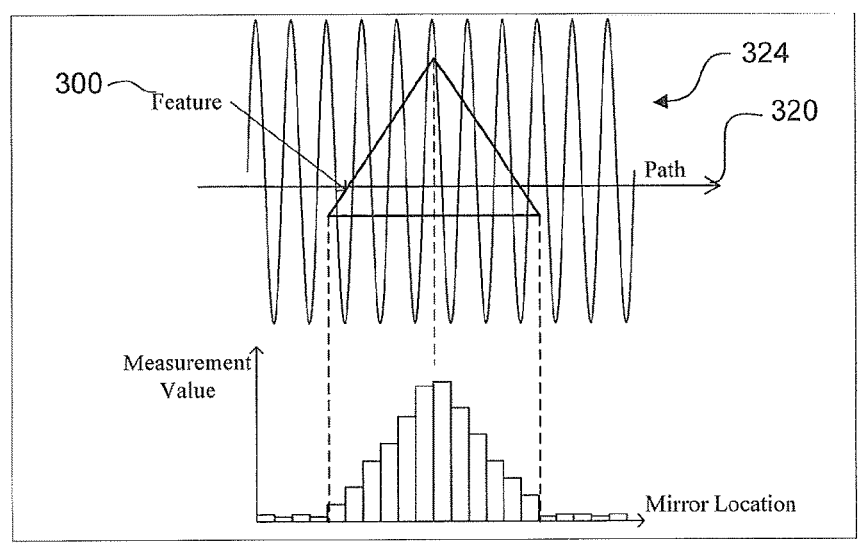

FIG. 10A and FIG. 10B illustrate an example position detection method where the scan path oscillation amplitude is made relatively large, i.e., about as large as or larger than the size of (i.e., at least one dimension of) feature 300. This allows for the general scan path 320 to be loosely selected because the relatively large size of the scan path oscillations is more likely to overlap a feature 300 or a portion thereof. Thus, if scan path 324 only partially overlaps feature 300, the measured feature profile can still approximately show the feature, and for certain features will allow for determining a center based on an edge-to-edge measurement. With respect to FIG. 10A, the centroid of the peak measures the (one-dimensional) location of the circular feature 300. The same can be done with features having other shapes, such as triangles (see FIG. 10B), diamonds, etc.

The position detection method using a relatively large scan path oscillation works particularly well for regularly shaped (e.g., symmetric) features 300 having known orientations, where the centroid measurement will provide sufficient information to locate the feature. Finding the centroid is more easily and accurately determined for features having a measurement value vs. mirror location plot that is more flat (e.g., FIG. 10A) than for features where the plot has substantial variation (e.g., FIG. 10B) due to the feature shape. Increasing the number of measurements (e.g., detector sampling) increases the measurement accuracy for determining the position of the center of feature 300.

With reference to FIG. 10B, note that oscillating scan path 324 completely covers feature 300 and the resulting measurement plot (measured feature profile) has a peak. The centroid of the peak measures the (one-dimensional) location of the feature far more precisely than any type of edge detection. In this instance, scanning in the y-direction (i.e., the addition of the oscillation to the scan path) is unnecessary.

Figure 11:
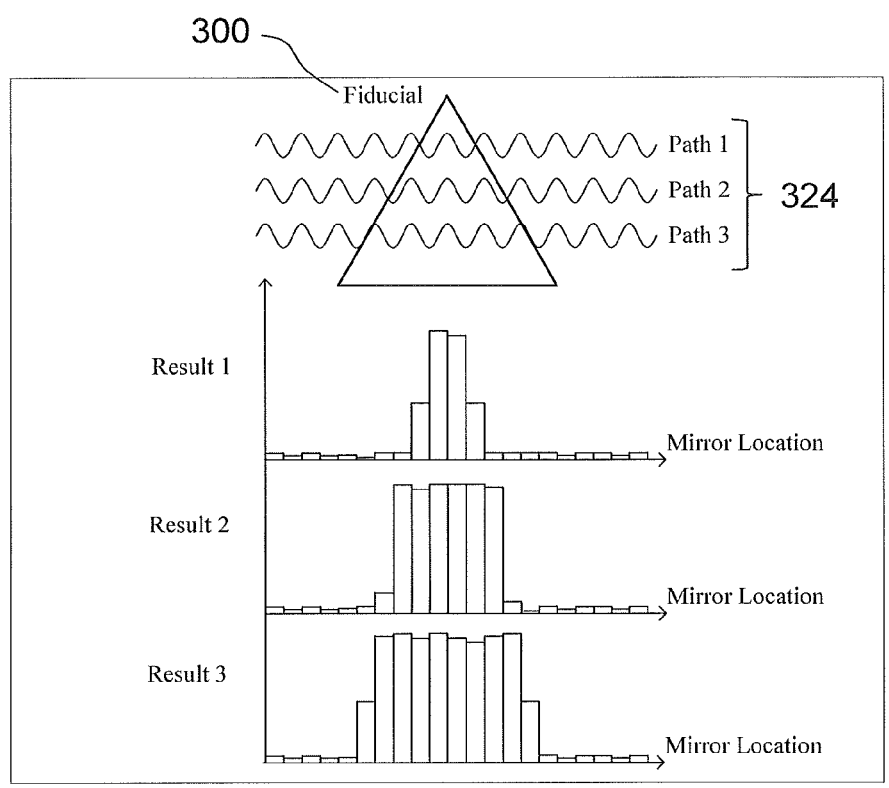
FIG. 11 illustrates an example of the position detection method that employs a shaped feature.

FIG. 11 illustrates an example of the position detection method that employs a shaped feature 300, which are most likely to be fiducials rather than biosensors or biosensor wells. Shaped features 300 such as triangles can provide information about how far scan path 324 is from the feature center in the direction perpendicular to the path. By examining the results from scan paths 1, 2 and 3, the scan path that yields the feature center can be deduced.

Figure 12:
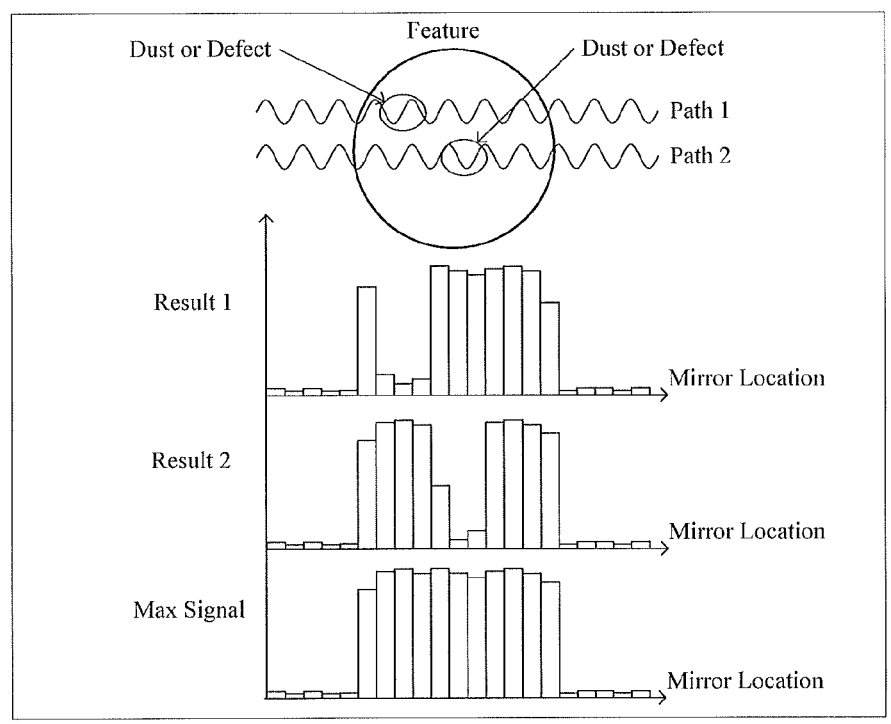
FIG. 12 illustrates an example position detection method where multiple scans of the object can be used to create multiple measured feature profiles that are combined to produce a final measured feature profile having optimal shape (maximum signal) relative to the actual feature profile.

In cases where dust or defects 301 on a feature 300 interfere with the scanning profile, an aggregate scanning profile can be formed by mathematically combining the results of one or more cross sectional measurements. An example of this approach is illustrated schematically in FIG. 12.

Figure 13A:
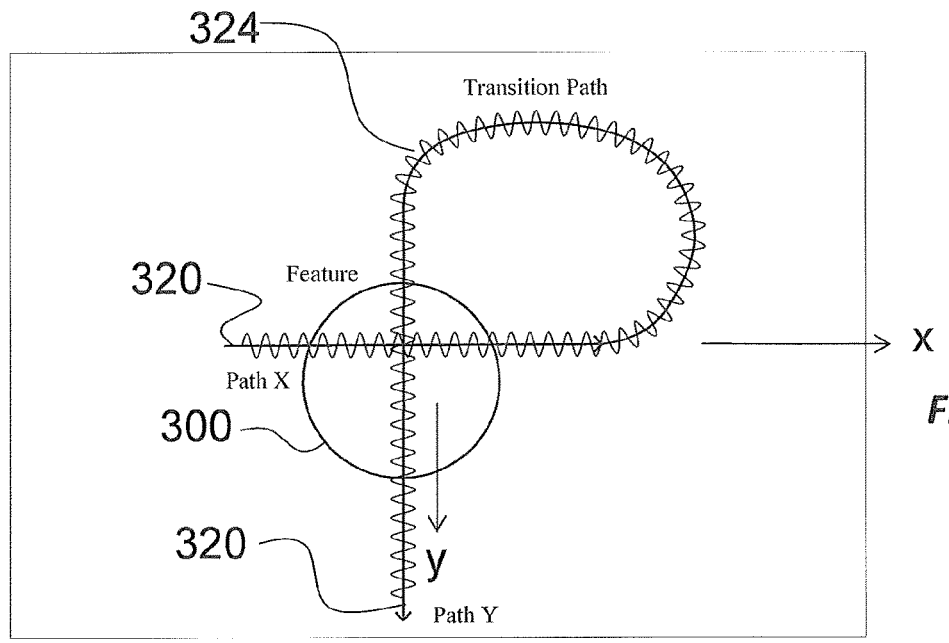
FIG. 13A and FIG. 13B illustrate an example position detection method that is useful for coarse initial detection of position-detecting features when the location of the sample feature is only generally known.
Figure 13B:
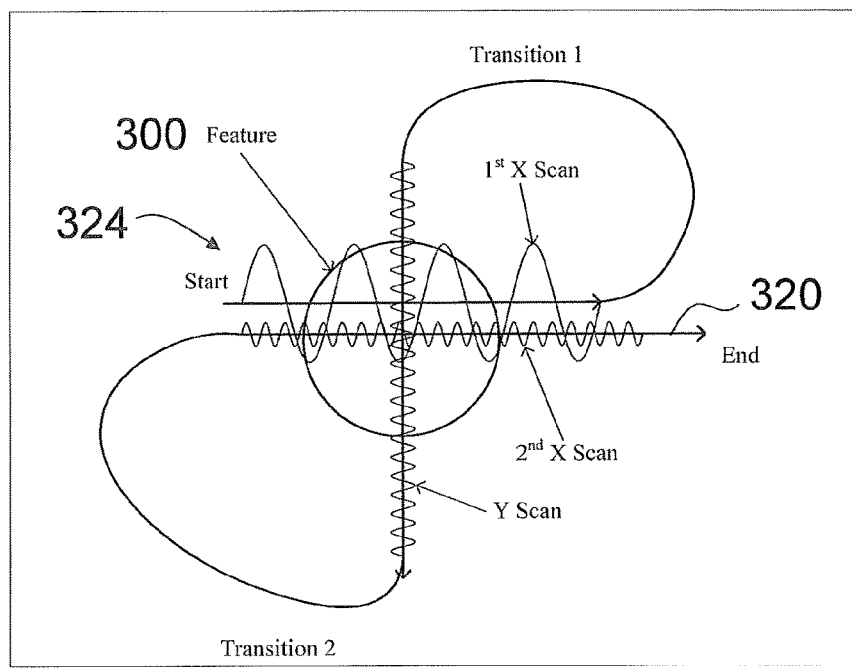

FIG. 13A and FIG. 13B illustrate an example position detection method that is useful for coarse initial detection of features 300 when the location of the sample feature is only generally known. In the method, beam spot 135 is traced over an oscillating scan path 324 having a relatively small amplitude. Oscillating scan path 324 is shown as crossing feature 300 slightly center in FIG. 13A and in a general scan path 320 in the x-direction. When feature 300 is found, oscillating scan path 324 is automatically changed so that the oscillating scan path has a general scan path in the y-direction so that feature 300 is scanned in the (in-plane) perpendicular direction.

With reference to FIG. 13B, another x-y scanning method of position detection is to first scan along the x-path with an oscillating scan path 324 having relative large oscillations. This type of oscillating scan path 324 has a high probability of hitting feature 300 but will not generally allow for finding the feature center location directly with any accuracy. However, once the presence and rough position of feature 300 has been identified, subsequent searches with less amplitude (or no amplitude) can be employed. As shown in FIG. 13B, an oscillating scan path 324 having a medium-sized oscillation and a general scan path 320 in the x-direction passes relatively close to the feature center and finds the feature y-height with reasonable accurately. Then a finer x-scan can be performed using information from the previous scan and employing a smaller oscillation amplitude.

Figure 14A:
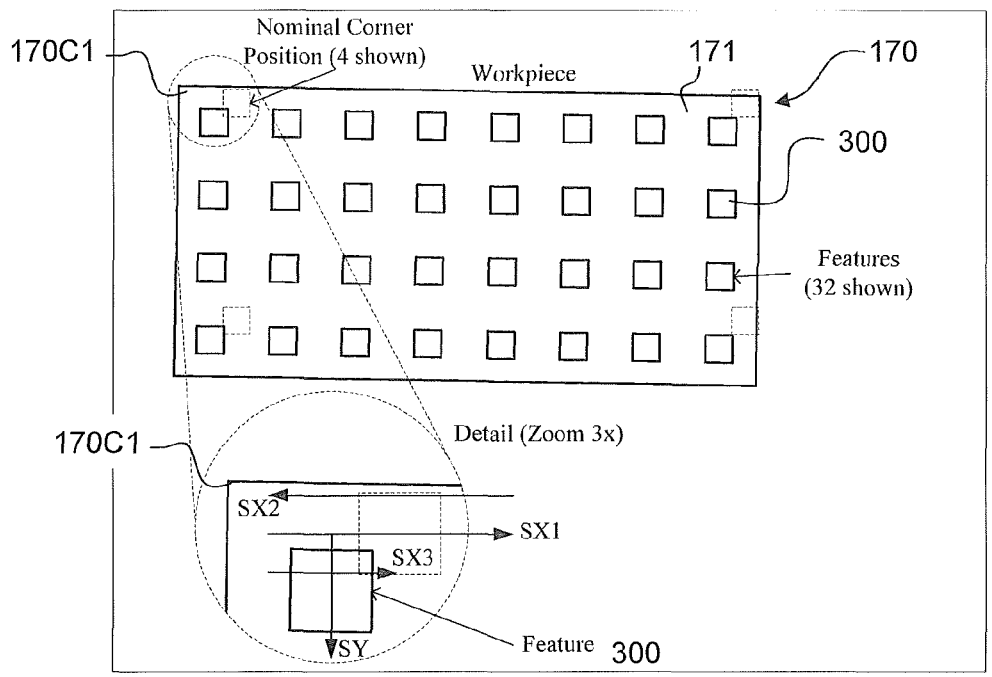
FIG. 14A and FIG. 14B are schematic diagrams that illustrate an example array of position-detecting features, with some features being near the microplate corners, in connection with an example position detection method that first measures a corner feature.
Figure 14B:
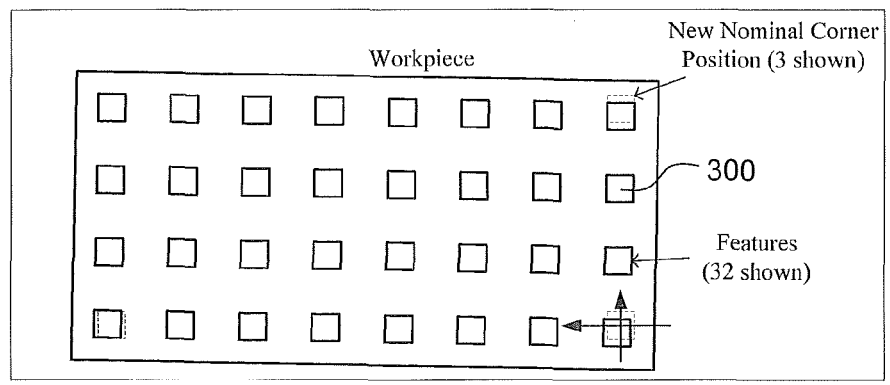

Another method of position detection involves detecting multiple features 300. FIG. 14A and FIG. 14B are schematic diagrams of a microplate that includes an array of features 300, including features near the microplate corners. Features 300 can be microplate wells W or fiducials 169 arranged on microplate surface 171 adjacent or in between adjacent wells. Features 300 are shown as being square by way of illustration. The method locates the position of microplate 170 and not just features 300. If the dimensions of a rectangular or square microplate 170 are well known (which is typically the case), the method can establish the positions of the features 300 on the microplate.

With reference to the inset of FIG. 14A, a first scan SX1 and a second scan SX2 in the x-direction are performed in the vicinity of one corner 170C1 of microplate 170. These x-direction scans are separated from each other by a distance about ½ that of the feature diameter. In both scans SX1 and SX2, the sought-after feature 300 was not found. Thus, a third scan SX3 (and possibly subsequent scans) is performed based on the results of the earlier scans. Once feature 300 is found (say, in scan SX3), this x-direction scanning can stop. At this point, the x-direction scan information is used to perform a scan SY in the y-direction that cuts through the middle of feature 300.

Once microplate corner 170C1 is located (or, corner feature 300 closest to corner 170C1 is located), the other corners (or corner features) can be located. Once one of the corner features is located, the other features can be readily located since their relative positions are known. An exact fit of the following form can be used with at least three pieces of feature measurement data (e.g. x and y for one corner, x or y for another).

A best fit of the same form is also straightforward with more than three pieces of data, for example the centers of all four corners.

$$\begin{bmatrix} x \\ y \end{bmatrix}_{ACTUAL} = \begin{bmatrix} \cos\theta & \sin\theta \\ \sin\theta & \cos\theta \end{bmatrix} \begin{bmatrix} x \\ y \end{bmatrix}_{NOMINAL} - \begin{bmatrix} x_0 \\ y_0 \end{bmatrix}$$

If translation and rotation of microplate 170 and apparent translation and scaling of the microplate due to a scale change of scanning mirror device 260 are considered, there are five unknowns (translation from the two effects can be combined). A general equation to which data can be fit is as follows. Five unknowns require five pieces of information for an exact solution. The x and y locations of two opposing corners plus the x or y location of one of the others is sufficient for a solution.

$$\begin{bmatrix} x \\ y \end{bmatrix}_{ACTUAL} = \begin{bmatrix} \cos\theta & \sin\theta \\ \sin\theta & \cos\theta \end{bmatrix} \begin{bmatrix} s_x & 0 \\ 0 & s_y \end{bmatrix} \left( \begin{bmatrix} x \\ y \end{bmatrix}_{NOMINAL} - \begin{bmatrix} x_0 \\ y_0 \end{bmatrix} \right)$$

An alternative is to use the general linear form. Even if the equation above has six unknowns, solving it requires six pieces of information. The x and y locations of three corner features are a good choice. In an example, all four corners are found for a best fit using a linear regression.

In an example, the position detecting methods employ an f-theta optical configuration such as shown in FIG. 5 and FIG. 6. The detector used may be photodetector 160, or alternatively spectrometer 140 can be employed as the photodetector since this includes an array of integrating photodetectors that each sample a narrow bandwidth of light. The methods detailed herein are structured to make use of the spectrometer's integrating ability, and to overcome its speed limitations. Integration can be performed optically where possible, or numerically i.e., sampling rapidly with respect to the sine-wave scan path 324, and combining the samples in an external system.

Examples of the position detecting methods described herein are capable of locating microplate 170 to within 0.025 mm in translation, rotation and linear deformation in approximately two seconds. This allows for scanning optical system 130 to accurately place beam spot 135 on biosensor 102, and in particular accurately scan the beam spot over each biosensor in a very controlled manner to obtain accurate readings.

Optical Reader System Calibration

With reference again to FIG. 8, the position of a point p on microplate 170 relative to perpendicular is given by $p = d \cdot \tan(\theta)$ where $\theta$ now refers to the tilt angle of the mirror (scanning mirror device 26) and d is the distance from the mirror to the surface at the optical center ($\theta = 0°$) and where $\theta$ is a small angle, $p \approx k \cdot \theta$.

This approximation worsens as angle $\theta$ increases, leading to distortion near the edges of the lens field. That is, a small change in angle $\theta$ results in a certain change in position on microplate 170, but the same small change in angle at the extremities of the microplate causes a larger change in position. The result is that the size of features 300 appears to increase with distance away from the optical axis. This causes position errors of incident beam 134I and thus error locations in the placement of beam spot 135 relative to biosensors 102 during the biosensor measurement process. It also leads to reduced accuracy in determining the position of microplate 170.

Thus, an aspect of the disclosure is calibrating system 100 to account for the aforementioned distortion to correctly position incident beam 134I and thus accurately position beam spot 135. The calibration involves properly identifying the angle $\theta$ required to achieve a given position on microplate 170. In particular, the angle $\theta$ is given by $\theta = \arctan(p/d)$. Note that for an f-theta lens with a focal length f, the distance $d = f$.

Figure 15:
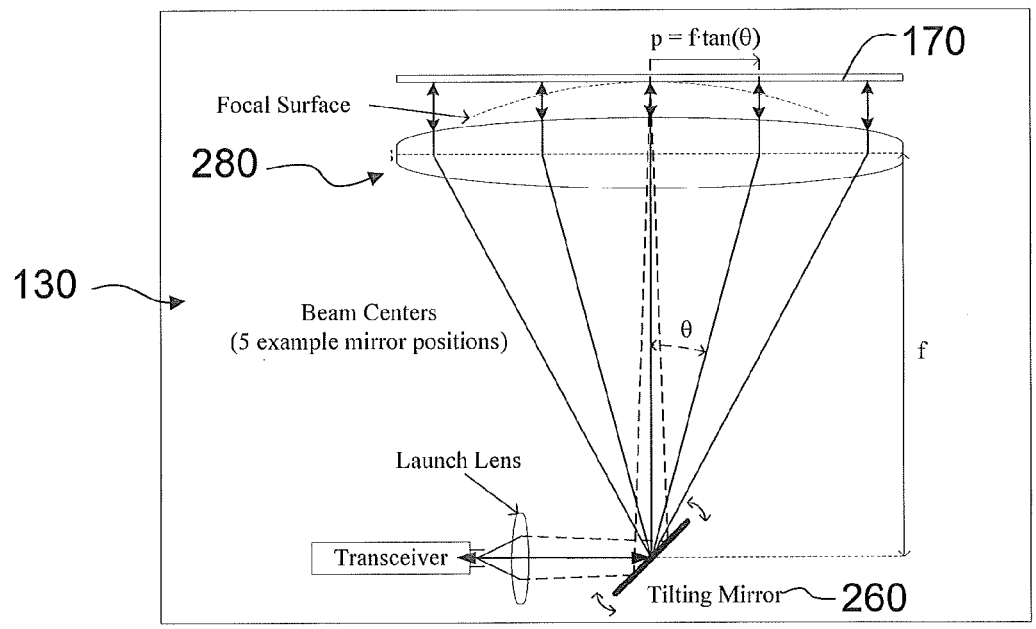
FIG. 15 is a schematic diagram of an example scanning optical system similar to that shown in FIG. 5.

FIG. 15 is a schematic diagram of an example scanning optical system 130 similar to that shown in FIG. 5 and FIG. 6. An objective lens 280 (i.e., an f-theta lens) is placed between microplate 170 and scanning mirror device 260, with the focal point of the objective lens located at the center of rotation of the mirror of scanning mirror device 260. Scanning optical system 130 exhibits the aforementioned tangential distortion, with the beam position on the sample being $p = f \cdot \tan(\theta)$, where f is the focal length of the f-theta objective lens 280.

Figure 16:
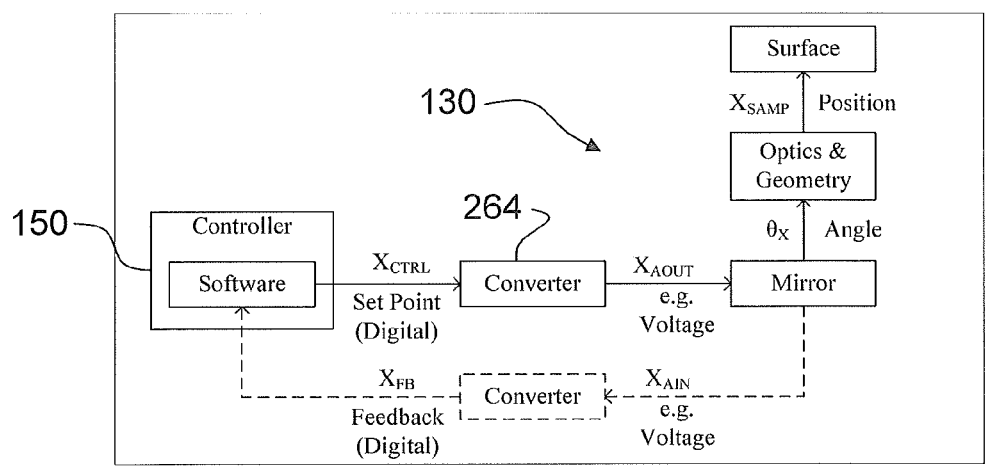
FIG. 16 is a schematic diagram of an example control system where a control variable in the controller (e.g., microplate positions in controller coordinates) is converted to an actual measured parameter (e.g., microplate positions in microplate coordinates)

FIG. 16 is a schematic diagram of an example control system where a control variable in the controller 150 (e.g., microplate positions in controller coordinates) is converted to an actual measured parameter (e.g., microplate positions in microplate coordinates). A digital control signal from software stored in controller 150 goes through a converter (e.g., mirror driver 264) to become analog power (i.e., an analog power signal) that drives the mirror of scanning mirror device 260 to a specific angle. The angle of input light beam 134I is determined by the mirror angle. Input light beam 134I goes through scanning optical system 130 and forms beam spot 135 at a corresponding position at microplate 170.

Embodiments of scanning optical system 130 can also have feedback from the mirror. This feedback also goes through a second converter (dashed-line box) and presented to the controller 150 in a digital format and is processed by the aforementioned software (i.e., instructions embodied in a computer-readable medium in the controller).

In the control system illustrated in FIG. 16, there are potential non-linearities in every block shown, with some of the non-linearities being more significant than others. The non-linearities can be small in the converters, for example, depending on their design. For MEMS mirrors, the relationship between input and output beam angle can have substantial non-linearity, with example MEMS mirrors being linear only to above 5%. Additionally, in 2-dimensional mirrors, there may be interaction between axes so that axis calibration cannot be done separately.

Thus, even if optics were used to correct for the above-described geometric and optical distortions, the MEMS mirror would defeat the purpose. Consequently, short of making a custom lens matching every MEMS mirror, a hardware solution directed to substantially eliminating distortions in a MEMS-based optical reader is problematic.

To perform a software-based method of calibrating system 100, the following functions are defined: (i) a control output function that specifies control output $(X_{CTRL}, Y_{CTRL})$ from desired static positions $(X_{SAMP}, Y_{SAMP})$, where $X_{SAMP}$ and $Y_{SAMP}$ are (x,y) positions at microplate 170; (ii) a control dither function that specifies control dither output $(A_{CTRL}, B_{CTRL})$ from desired sample sizes $(A_{SAMP}, B_{SAMP})$ at static points $(X_{SAMP}, Y_{SAMP})$ on microplate 170. For multiple dither frequencies, multiple control dither functions—one for each frequency—are required. Here, "sample" means in one embodiment a microplate having one or more biosensors.

For the most accurate calibration to take place, the drive frequency of scanning mirror device 260 is accounted for because the calibration differs at different drive frequencies.

For effective calibration to occur, the relationship between the control quantities $(X_{CRTL}, Y_{CRTL})$ (controller coordinates) and the sample quantities $(X_{SAMP}, Y_{SAMP})$ (sample coordinates) (and also between the feedback at the controller $(X_{FB}, Y_{FB})$ and sample coordinates if feedback is employed) need to be determined to create correction maps (functions). These functions are necessary in finding the control setting required to move to a particular position on the sample $(F_1)$ and finding the position on the sample from the feedback $(F_2)$ as denoted by the equation below.

$$(X_{CRTL}, Y_{CRTL}) = F_1\{(X_{SAMP}, Y_{SAMP})\}$$

$$(X_{SAMP}, Y_{SAMP}) = F_2\{(X_{FB}, Y_{FB})\}.$$

Function F1 drives scanning mirror device 260 to obtain an accurate (non-distorted) location of beam spot 135 on microplate 170. Function F2 is used to calibrate the feature coordinates with feedback coordinates from scanning optical system 130 and in particular from scanning mirror device 260 and mirror driver 264.

Figure 17A:
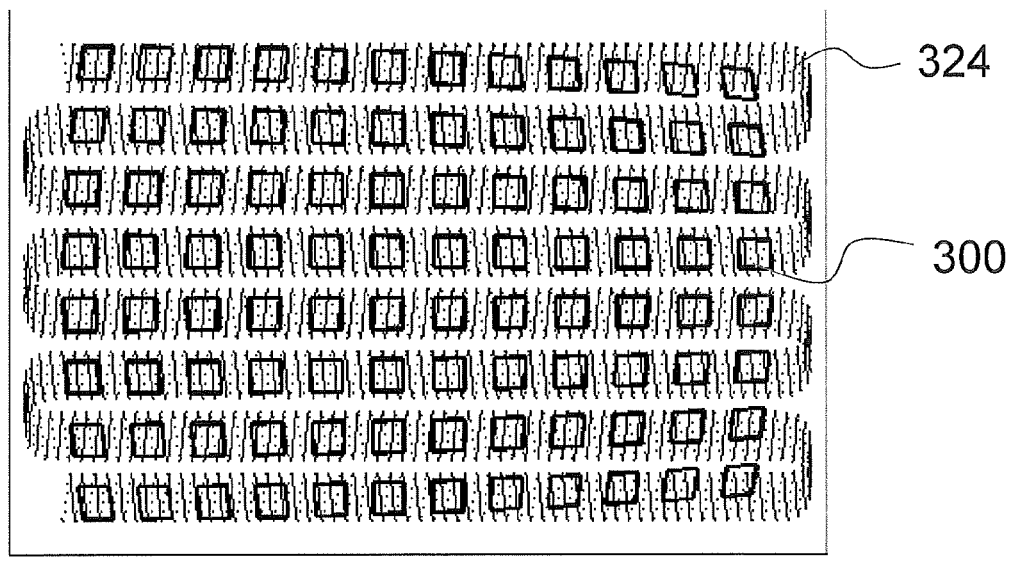
FIG. 17A and FIG. 17B are schematic diagrams of the position-detecting features plotted along with the beam spot scan paths, illustrating how non-linearities in the optical reader can give rise to spatial distortion of the microplate coordinates.
Figure 17B:
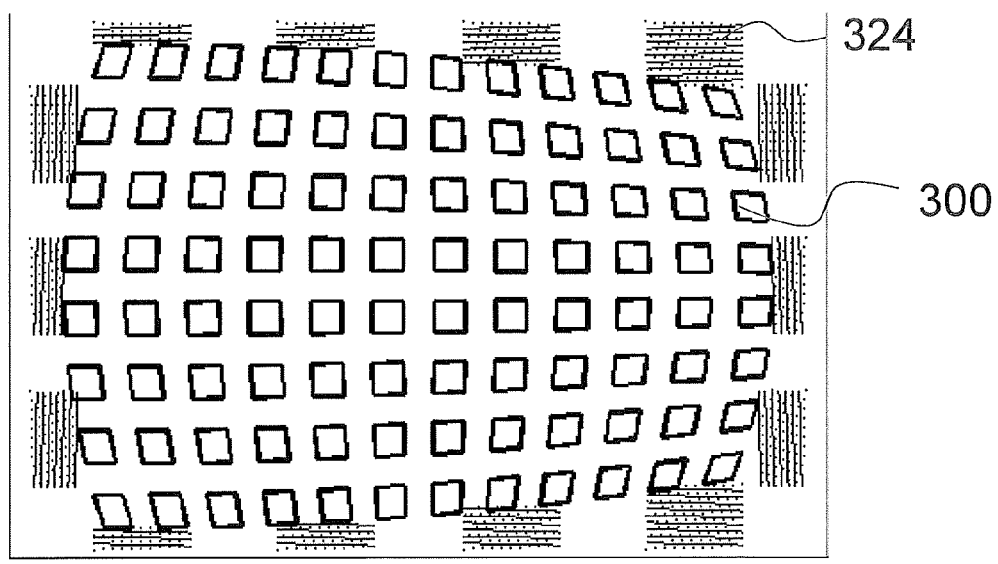

FIG. 17A and FIG. 17B are schematic diagrams of the position-detecting features plotted along with the beam spot scan paths, illustrating how non-linearities in the optical reader can give rise to spatial distortion with respect to the actual microplate coordinates. FIG. 17A also schematically illustrates how a calibration sample is derived in the controller's coordinates $(X_{CRTL}, Y_{CRTL})$. If the distortion is not too large, the X centers of features 300 can readily be detected with 1-D horizontal scans as described above, and calibration can be performed directly. The X coordinate centers in FIG. 17A have been found, but because of the aforementioned non-linearities of system 100, the calibration sample appears distorted.

If the distortion is too large, a straight line cannot go through all the features in one row without touching features in other rows. FIG. 17B is similar to FIG. 17A but with a larger amount of distortion. In the event of such large distortion, the scanning optical path 324 for locating the position of features 300 can be modified to find the border or part of the border. FIG. 17B scan paths 324 can be used to search in either the horizontal or diagonal directions where the amplitude of oscillation must be at least the size of the largest expected gap between features in the search region. This is to allow an estimated calculation of the sample's shape outline.

The calibration method corrects distortion observed in the X path (but not in the Y path) that is caused by the mirror tilt in scanning mirror device 260 when the input light beam 134I turns 90°. The distorted image of FIG. 17B appears to shrink from left to right. With this pattern type, locating the outside dimension or centers of the corner features in Y is sufficient to find search paths that pass through all features in the top and bottom rows. The other rows are interpolated between the top and bottom. If the distortion is barreled in the center (as it is for X), the known location of a point half-way along the row is needed for curvilinear (e.g., parabolic) interpolation instead of linear interpolation.

This information is available from "windowing," as shown in FIG. 17B. The results are points $(X_{CRTL}, Y_{CRTL})$ that match known locations $X_{SAMP}$ such as edges or center points. At this stage, an intermediate calibration can be done since $Y_{SAMP}$ is still unknown. An intermediate transformation equation is defined as $X_{CRTL} = G(X_{SAMP}, Y_{CTRL})$.

Figure 18A:
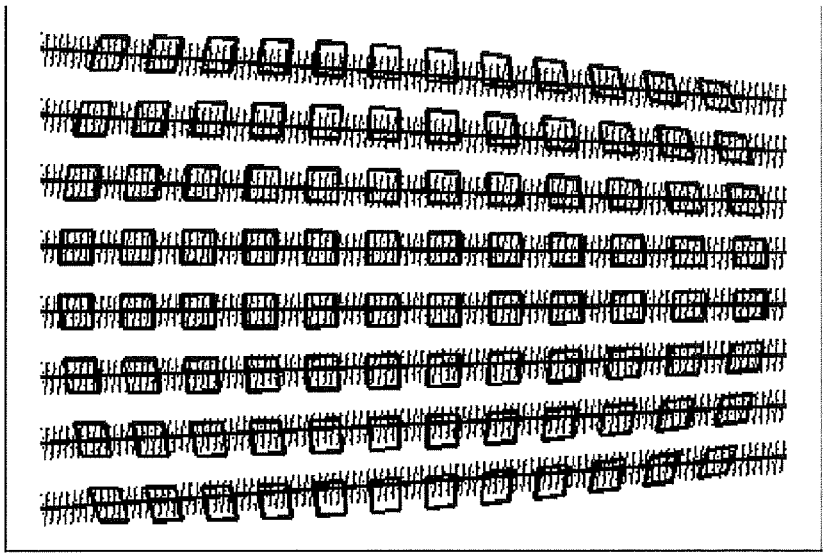
FIG. 18A and FIG. 18B example scan paths that account for the distortion of the microplate coordinates.
Figure 18B:
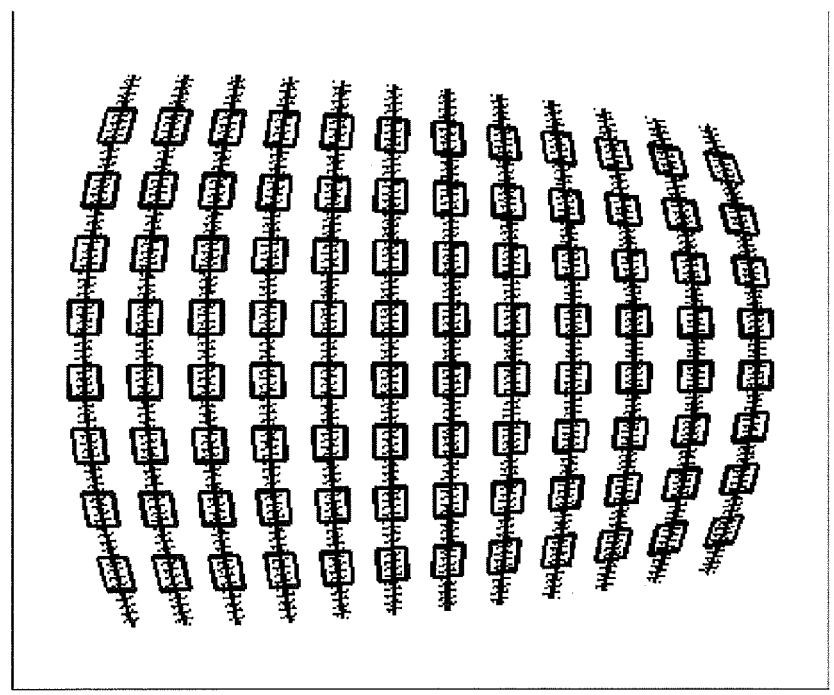

FIG. 18A and FIG. 18B illustrate example scan paths that account for the distortion of the microplate coordinates. FIG. 18A shows an example of the interpolation from previously found y-center locations for the four corner calibration features. By using the intermediate equation, for any mirror location $Y_{CTRL}$ one can move to the desired X location on the plate $(X_{SAMP})$ by finding $X_{CRTL}$. FIG. 18B schematically illustrates another example calibration method that involves performing 1-D searches made to the y-centers where the x-centers are known. This works even if the sample is placed in a tilted holder. In this case, the method just interprets the distortion and corrects for it.

If the nominal locations of position-detecting features 300 follow some other pattern, one can still generate a path that goes through their approximate locations if $Y_{CTRL}$ is found using the method in FIG. 18A. The results are points $(X_{CRTL}, Y_{CRTL})$ that match known locations $(X_{SAMP}, Y_{SAMP})$ such as edges or center points. The calibration can now be completed.

It is noted that when there is feedback and ($X_{FB}$, $Y_{FB}$) are known, these coordinates match known the locations ($X_{SAMP}$, $Y_{SAMP}$) because they can be recorded every time an edge or a center is found.

Figure 19A:
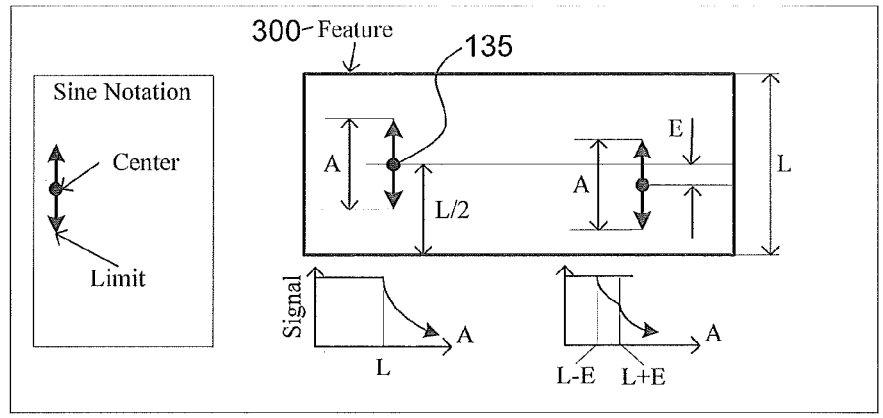
FIG. 19A and FIG. 19B are schematic diagrams that illustrate two related calibration techniques based on driving a beam spot with a sine-wave driving frequency.
Figure 19B:
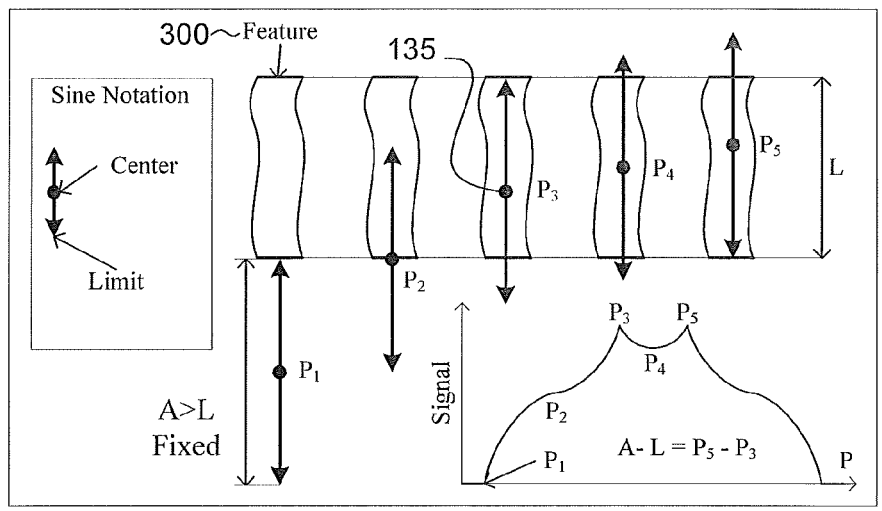

FIG. 19A and FIG. 19B are schematic diagrams that illustrate two related calibration techniques based on driving a beam spot with a sine-wave driving frequency. FIG. 19A illustrates an example calibration technique that involves scanning beam spot 135 over feature 300 with a sine-wave driving frequency provided to scanning mirror device 260. The calibration scanning involves placing beam spot 135 in the center of the feature 300 of known size, and then scanning the beam spot in a given direction with varying amplitude until the return signal (reflected beam 134R) starts to decrease. Since MEMS mirrors have non-linear dynamics a 1-volt change that moves the mirror by 1 mm does not guarantee a 1 volt sinusoid at say, 500 Hz, will result in a 1 mm oscillation. It could be much larger or smaller, depending on the mirror and the frequency. The mirror needs to be calibrated at each oscillation frequency at which the mirror will be driven.

With feedback, a sinusoidal control of known size is produced to observe the feedback. The feedback can then be converted to sample units, and the relationship for a sinusoid at that point is produced. This can be done in an X and Y grid, and with oscillation in both X and Y to complete a detailed map. Without feedback, features of known size are needed to perform the calibration.

FIG. 19B shows another method for calibrating a sine-wave driving frequency. A feature 300 of known size was used. The sine-wave oscillation imparted to beam spot 135 needs to be larger than a dimension of the feature. Beam spot 135 is scanned in the same direction as the oscillation, resulting in a signal profile as a function of spot position that has two peaks, as shown in the "signal vs. P" plot. It is much easier to find the center of a peak than a point at which power decreases.

Once the two peaks are established, the difference in their positions is also the difference in the size of the sine wave versus the feature. If the feature size is known, the sine-wave size can be deduced. This should be done in X and Y at multiple locations to acquire enough data about how the sinusoid varies. Alternatively, this method can be carried out in a single location (e.g., at the feature center) if the scale does not change too much with position on the plate.

It will be apparent to those skilled in the art that various modifications to the preferred embodiment of the disclosure as described herein can be made without departing from the scope of the disclosure as defined in the appended claims. Thus, the disclosure covers the modifications and variations provided they come within the scope of the appended claims and the equivalents thereto.

What is claimed is:

1. A method of determining the position of a microplate having a surface and that supports one or more biosensors in an optical reader system, the method comprising:

scanning a beam spot over a scan path over a portion of the microplate surface, the scan path having a first general direction and an oscillating component in a second direction perpendicular to the first general direction and imparted by a scanning mirror device having an adjustable orientation, thereby defining a two-dimensional scan path;

passing the oscillating component of the two-dimensional scan path over at least a portion of a position-detecting feature of the microplate and generating reflected light from the position-detecting feature;

detecting the reflected light as a function of the scanning mirror device orientation to establish a measured profile of the position-detecting feature; and determining, from the measured profile, a center of the position-detecting feature.

2. The method of claim 1, further comprising performing the detecting using a spectrometer of the optical reader system.

3. The method of claim 1, further comprising the scanning mirror device including a micro-electro-mechanical system (MEMS) mirror.

4. The method of claim 1, further comprising performing multiple scans of the beam spot over multiple two-dimensional scan paths having different amplitudes of the oscillating component.

5. The method of claim 1, further comprising the oscillating component of the two-dimensional scan path having an amplitude that is at least as large as a dimension of the position-detecting feature.

6. The method of claim 1, further comprising directing light that forms the beam spot on the microplate through an f-theta lens arranged between the scanning mirror device and the microplate.

7. The method of claim 1, wherein the position-determining feature comprises a fiducial or a biosensor well.

8. The method of claim 1, further comprising determining the center of the position-determining feature by calculating a centroid of the measured profile.

9. The method of claim 1, further comprising:

determining a position of the microplate based on the determined center of the position-detecting feature; and optically reading the least one biosensor based on the determined position of the microplate.

\* \* \* \* \*